(12) United States Patent
Jablonski

(10) Patent No.: US 8,092,825 B2
(45) Date of Patent: Jan. 10, 2012

(54) GLYCAN BINDING PROTEINS AS THERAPEUTIC TARGETS FOR RETINAL DISORDERS AND TREATMENT METHODS BASED THEREON

(75) Inventor: Monica M. Jablonski, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 790 days.

(21) Appl. No.: 12/057,599

(22) Filed: Mar. 28, 2008

(65) Prior Publication Data

US 2009/0060980 A1    Mar. 5, 2009

Related U.S. Application Data

(60) Provisional application No. 60/920,700, filed on Mar. 29, 2007.

(51) Int. Cl.
| | |
|---|---|
| *A61K 9/00* | (2006.01) |
| *A61K 31/702* | (2006.01) |
| *G01N 33/53* | (2006.01) |
| *G01N 33/566* | (2006.01) |
| *A61P 27/02* | (2006.01) |

(52) U.S. Cl. ............ 424/428; 514/42; 435/7.1; 436/501
(58) Field of Classification Search ........................ None
See application file for complete search history.

(56) References Cited

U.S. PATENT DOCUMENTS

| | | |
|---|---|---|
| 2003/0157161 A1 | 8/2003 | Hunter et al. |
| 2006/0210604 A1 | 9/2006 | Dadey et al. |

OTHER PUBLICATIONS

Schmidt-Erfurth. "Management of neovascular age-related macular degeneration" Progress in Retinal and Eye Research 26 (2007) 437-451.*
Tulsiani DRP et al., J. Biol. Chem. vol. 258, No. 12:7578-7585, Jun. 25, 1983.
Wang X et al., Neuron Glia Biol. vol. 1:1-9, Jan. 2005.
International Search Report and Written Opinion for corresponding International Application PCT/US2008/58576.
Jingshen TUO et al. Murine Ccl2/Cx3cr1 Deficiency Results in Retinal Lesions Mimicking Human Age-Related Macular Degeneration, Invest. Ophth. Vis. Sci. vol. 48, Aug. 2007.

* cited by examiner

*Primary Examiner* — Robert A Wax
*Assistant Examiner* — Danah Al-Awadi
(74) *Attorney, Agent, or Firm* — McLaren Legal Services; Margaret J. McLaren, Esq.

(57) ABSTRACT

Disclosed are novel methods of treatment for retinal diseases and conditions including age-related macular degeneration, genetic-based retinal degenerations and retinal detachment. A novel glycan binding protein thought to be a cell surface receptor has been discovered in the retina. The retinal glycan binding receptor is shown to play an important role in promoting assembly of outer segment (OS) membranes by the photoreceptor cells of the eye, a process that is essential for vision. Based on the finding that certain sugars can bind with very high affinity to the retinal glycan receptor and stimulate its function, the invention provides novel therapeutic agents for treatment of retinal diseases that are multivalent N-linked glycans. Preferred pharmaceutical compositions in accordance with the present invention comprise active agents having the general formula: $(Gal-GlcNAc)_n-Man_3-GlcNAc_2$, where n is 1-4. Particularly preferred multivalent glycans are galactosylated, biantennary (NA2), and asialo, galactosylated, triantennary (NA3) oligosaccharides.

13 Claims, 16 Drawing Sheets

FIGS. 1A-D

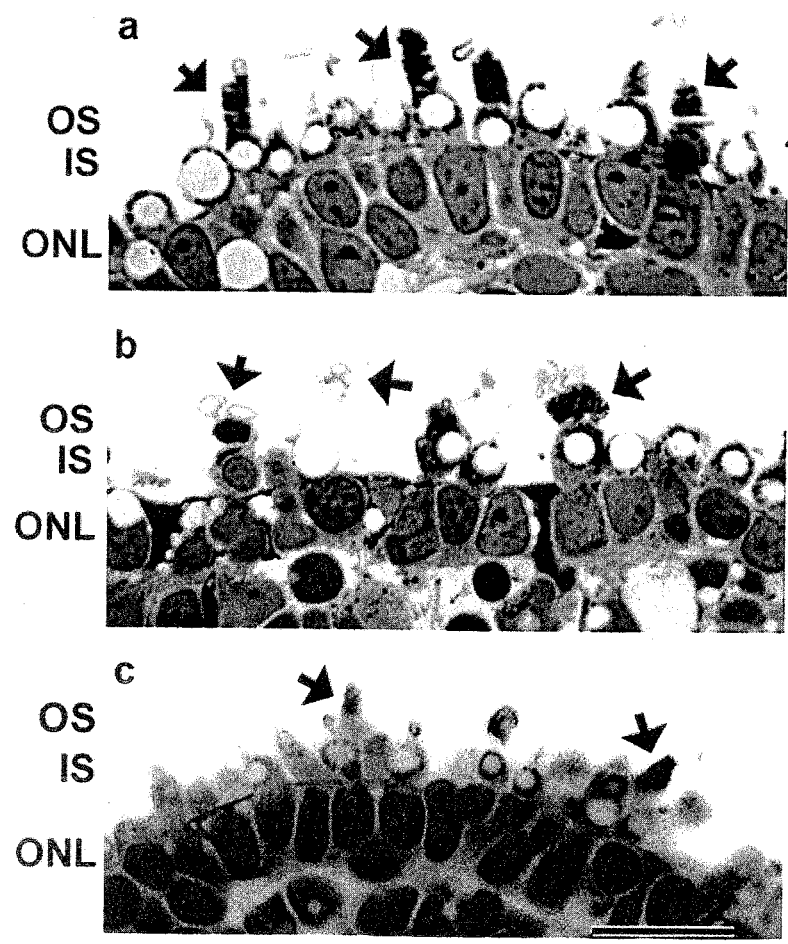
FIGS. 10A-C
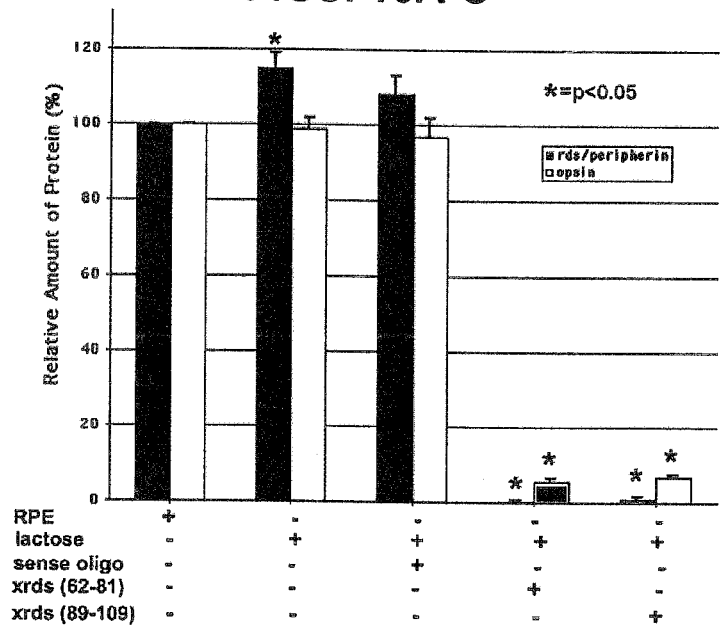
FIG. 10D

GLYCAN BINDING PROTEINS AS THERAPEUTIC TARGETS FOR RETINAL DISORDERS AND TREATMENT METHODS BASED THEREON

CROSS-REFERENCE TO RELATED APPLICATIONS

The present application claims the benefit of priority under 35 USC §111(e) to U.S. Provisional Application No. 60/920,700 entitled "Glycan Binding Proteins, Methods of Isolation and Uses Thereof," filed Mar. 29, 2007, which is hereby incorporated by reference in its entirety.

FIELD OF THE INVENTION

The invention relates generally to glycan-binding proteins, methods for isolating these proteins, and treatment methods based on these proteins. More particularly, the invention relates to novel treatment methods using glycan ligands that bind with high affinity to glycan-binding proteins that are important therapeutic targets, e.g., in disorders of the eye such as age-related macular degeneration and retinitis pigmentosa.

BACKGROUND OF THE INVENTION

A wide array of blinding and visually impairing disorders is caused by degeneration of the photoreceptors of the retina. The retina is a complex structure comprising several layers of neuronal cell types, as well as the Müller glia, and the adjacent RPE. Photoreceptors are structurally polarized neurons with several unique features. At one pole of the neuron is the chemical synapse; at the other end is the outer segment (OS), the most highly specialized region of the photoreceptor cell. Vision begins at the level of the photoreceptor OS.

Functional and anatomical integrity of the OS is essential for proper light detection and optimal vision. As seen by electron microscopy, the OS comprises an array of up to 1,000 flattened stacked membranous saccules or "discs" in perfect register, surrounded by a plasma membrane (2, 3). The membranous discs are continuously renewed at the proximal end of the OS, and the distal ends of the OS are shed and phagocytized daily by the adjacent layer of cells known as the retinal pigmented epithelium (RPE) (1). Several of the steps that lead to formation and organization of OS have been elucidated; however the chain of events that regulates OS assembly remains incompletely characterized.

The health and survival of the photoreceptors are heavily dependent on the integrity of other surrounding cell types of the retina, including RPE cells and the Müller cells. The importance of an intact and fully functional RPE on photoreceptor development and survival has long been recognized. In addition to its role in phagocytosis (1), the RPE is necessary to support photoreceptor OS development and differentiation (4). RPE-secreted proteins including pigment epithelium-derived factor (PEDF) promote photoreceptor differentiation and survival (5-9). At present, the nature of the RPE-produced factors that are necessary for morphogenesis of the photoreceptors is beginning to be elucidated.

The Müller cells of the retina are also recognized to play important roles in photoreceptor development and survival. Müller cells are coupled embryologically, physically, and metabolically to photoreceptors (10). It has been proposed that Müller cells provide trophic support to promote photoreceptor survival (10-12) and may regulate synaptogenesis (13, 14) and neuronal processing (15) through bidirectional communication (16). During development, Müller cells, photoreceptors and a subset of inner retinal neurons originate from a single retinal progenitor and arrange themselves in a columnar fashion (10, 17) in which Müller cells surround photoreceptors from the synaptic terminals to the inner segments (18), where the two cells are connected via the adherens junctions that comprise the outer limiting membrane of the retina (reviewed in (19) and (20)). In addition, Müller cells express voltage-gated ion channels, neurotransmitter receptors and various uptake carrier systems which enable them to modulate the activity of retinal neurons (21). Targeted disruption of Müller cell metabolism with α-aminoadipic acid results in disorganization of OS both in RPE-supported retinas and in RPE-deprived retinas exposed to IPTG. Thus, it is believed that Müller cells interact with photoreceptors through mechanisms that may regulate, at least in part, the assembly of OS membranes (22, 23).

Recently there has been recognition that specific glycans play important physiological roles in non-retinal tissues, e.g., functions related to innate immunity or parasitic adhesion. Recently, receptors specific for unique glycans have been cloned and partially characterized in several tissues (24-30). In the liver, it has been shown that the affinity of the receptors for glycan ligands is markedly enhanced for multivalent ligands, suggesting that the clustering of terminal sugar residues promotes strong receptor-ligand interactions (24, 25, 27, 28, 31, 32). Recent publications have documented the discovery of Dectin-1, a novel β-glucan receptor, and its role in modulating the immune system response by inducing leukocyte activation and the production of mediators of inflammation (26, 29, 30). Additionally, mannose-binding receptors have been cloned and characterized in *Acathamoeba*, and shown to play a critical role in adhesion of the parasite to host cells (33).

There is general recognition that carbohydrates play a role in maintaining the integrity of the photoreceptor OS. It has been previously recognized that carbohydrates and their lectin receptors play an important physiological role in the retina. Carbohydrates have both a metabolic and a non-metabolic role in retinal physiology. The metabolic role of carbohydrates in the retina has been previously studied (34, 35). In addition to having metabolic functions in the retina, carbohydrates also play fundamental non-metabolic roles. For example, tunicamycin, an antibiotic that prevents the formation of N-linked oligosaccharides via the lipid intermediate pathway during protein glycosylation significantly alters membrane morphogenesis in adult *Xenopus* retinas, suggesting that the lack of sugar moieties on glycoproteins within the retina may be responsible for the misassembly of OS membranes (36-38). If post-translational trimming of oligosaccharides is inhibited with castanospermine, however, nascent disc morphology is identical to control conditions, suggesting that post-translational removal of oligosaccharides is not essential for normal disc morphogenesis (39).

Several sub-types of lectins, including lactose-binding lectins, have been localized to the retina (40-43). In addition, lectin-binding sites of the outer retina have been described (44-47). For example, a 16 kD galectin has been suggested to play a modulating role in the interactions between the RPE and the retina (48). Moreover, its presence throughout Müller cells suggests a role in metabolic processing between Müller cells and other retinal cells (48). Additionally, specific expression of galectin at the outer limiting membrane (OLM) underscores its probable role in mediating cell-cell interactions between Müller cells and photoreceptors. Involvement of galectin-1 in regulating the adhesion of photoreceptors and the outer plexiform layer has also been proposed (49).

The presence and uptake of several glycans of the A3 family has been demonstrated in the retina. In the rat, immunoreactivity for fetuin has been reported to be present during development in cells of the ganglion cell layer and in a small population of the cells in the neuroblastic layer (56). A wider distribution of retina-derived fetuin, in the RPE as well as in ganglion cells, photoreceptor inner segments, the outer plexiform layer and optic nerve processes has also been reported (57). Fluoresceinated alpha-fetoprotein is taken up exclusively by maturing neurons of the chick retina, rather than undifferentiated precursors or fully differentiated neurons, indicating that alpha-fetoprotein may play a role in retinal maturation. Together these studies demonstrate that members of the A3 family of glycans are present in the retina, and that the ligand-receptor complex is internalized in a manner that is similar to that demonstrated for the asialoglycoprotein receptors of the liver (58).

Despite these advances, the nature of the molecular signals that regulate photoreceptor OS assembly are not well understood at present. There is a clear need for better understanding of the mechanisms by which photoreceptor OS assembly occurs, is maintained, and breaks down in retinal diseases and disorders. It would be particularly desirable to identify and characterize glycan-binding proteins that mediate these essential processes in the retina, and to develop new therapeutic approaches and agents based thereon.

SUMMARY OF THE INVENTION

It has been discovered that a novel glycan-binding protein, believed to be a cell surface receptor, is involved in photoreceptor outer segment (OS) assembly in the retina. Stimulation of the retinal glycan receptor in a retinal explant assay system with a multivalent N-linked oligosaccharide ligand results in support of OS assembly at far lower concentrations than is possible using corresponding monovalent ligands, thus demonstating a very high affinity of the retinal glycan-binding protein for such multivalent ligands.

Accordingly, based on these discoveries, in one aspect the invention provides a method of treatment for a retinal disease or disorder. The method includes administering to a subject in need thereof a pharmaceutical composition comprising a therapeutically effective amount of a multivalent glycan. The multivalent glycan composition can provide beneficial effects such as promoting formation of photoreceptor OS membranes and promoting integrity of adherens junctions, e.g. those that anchor the photoreceptors in place within the retina.

In preferred embodiments of the method of treatment, the multivalent glycan is an N-linked oligosaccharide.

Multivalent N-linked oligosaccharides of use in the treatment method have the general formula $(Gal-GlcNAc)_n$-$Man_3$-$GlcNAc_2$ where n is 1-4.

In one embodiment, the multivalent glycan is a biantennary N-linked oligosaccharide such as an asialo, galactosylated, biantennary (NA2) oligosaccharide; an asialo, galactosylated, fucosylated, biantennary (NA2F) oligosaccharide; or a disialo, galactosylated, biantennary (A2) oligosaccharide.

In another embodiment of the method, the multivalent glycan ligand is a triantennary N-linked oligosaccharide selected from an asialo, galactosylated, triantennary (NA3) oligosaccharide; and a trisialo, galactosylated, triantennary (A3) oligosaccharide.

In yet another embodiment of the method, the multivalent glycan is a tetraantennary N-linked oligosaccharide such as an asialo, galactosylated tetraantennary (NA4) oligosaccharide.

In some preferred embodiments of the method of treatment, the composition is administered directly to the eye of the subject in need of treatment, for example by intraocular injection. Alternatively, the composition is administered in the form of a biodegradable matrix that over a period of time releases the therapeutic compound within the eye, following implantation of the matrix into the eye, e.g., in proximity to the retina or RPE.

Many forms of retinal diseases and disorders involve loss of integrity of OS membranes and therefore may be amenable to treatment with compositions and methods in accordance with the present invention. Exemplary conditions include but are not limited to genetic-based retinal degenerations including Leber's congenital amaurosis, age-related macular degeneration, and retinal detachments of any etiology.

A related aspect of the invention is a pharmaceutical composition suitable for administration to the eye comprising a multivalent N-linked oligosaccharide having the formula $(Gal-GlcNAc)_n$-$Man_3$-$GlcNAc_2$, where n is 1-4.

In one preferred embodiment, the composition is formulated in a pharmaceutically acceptable solution suitable for injection into the eye of a subject.

In another preferred embodiment, the composition is formulated in a biodegradable matrix suitable for implantation into the eye, and preferably for slow release of the therapeutic agent.

Yet another aspect of the invention is a method for isolating a retinal glycan-binding protein. The method includes the steps of:

(a) contacting a retinal cell or a mixture of proteins or fragments thereof derived from a retina with a ligand that is a multivalent N-linked oligosaccharide, under conditions that permit selective binding of the ligand to a glycan-binding protein or fragment thereof; and (b) isolating proteins that are selectively bound to the glycan ligand, thereby isolating one or more glycan-binding proteins expressed in the retina.

In a preferred embodiment of the method, the isolated glycan-binding protein is a cell surface receptor present on Müller cells that functions to promote the organization of OS membranes in photoreceptor cells.

In some preferred embodiments of the isolation method, the glycan ligand is a non-metabolizable sugar. Particularly preferred glycan ligands are multivalent glycans such as multivalent N-linked glycans. The structure of the N-linked multivalent glycan ligand can have the formula:

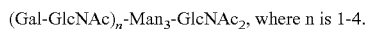

$(Gal-GlcNAc)_n$-$Man_3$-$GlcNAc_2$, where n is 1-4.

In various embodiments of the method of isolation, the multivalent glycan ligand is a biantennary, triantennary or tetraantennary N-linked oligosaccharide.

Particularly preferred multivalent ligands suitable for use in the isolation of a retinal glycan receptor that mediates photoreceptor OS assembly are asialo, galactosylated, biantennary (NA2), and asialo, galactosylated, triantennary (NA3) oligosaccharides that bind to this receptor with very high affinity.

Other aspects and advantages of the invention are further discussed below.

BRIEF DESCRIPTION OF THE DRAWINGS

FIG. 1C shows that 5 mM mannose fails to support the proper assembly of OS in the absence of RPE. In contrast, in the presence of 5 mM lactose. OS assembly is supported in the absence of the RPE layer.

FIGS. 10A-C are photographs showing light microscopic images of *Xenopus* retinas exposed to sense oligonucleotides (10A), and two antisense oligonucleotides (10B, C), complementary to nucleic acid sequence in the peripherin2 gene.

FIG. 10D illustrates the levels of opsin and rds/peripherin in *Xenopus* retinas exposed to antisense oligonucleotides complementary to nucleic acid sequence in the peripherin2 gene.

DETAILED DESCRIPTION OF THE INVENTION

Figure 1:
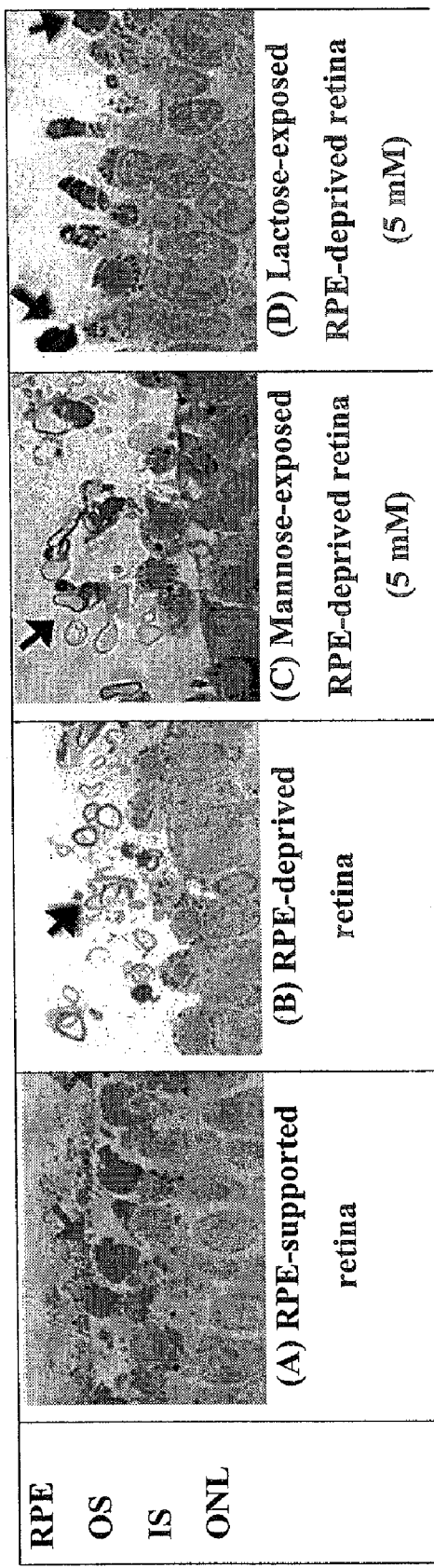
FIGS. 1A-D are four photographs showing an assay system for evaluating the effect of glycan compounds on assembly of photoreceptor outer segment (OS) membranes in vitro. Intact retinas are removed from stage 33/34 *Xenopus laevis* tadpoles and cultured. In some retinas (see, e.g., FIG. 1B), the RPE is gently removed from the underlying neuroepithelium; thus the OS (arrows) are elaborated in the absence of the RPE.

A novel glycan-binding protein associated with maintaining the integrity of the photoreceptors and promoting the normal structural organization of the outer retina has been discovered. Furthermore, ligands that bind to this receptor with extremely high affinity have been identified, and are disclosed herein. These findings provide inter alia the basis for the use of a novel class of drugs. i.e., multivalent N-linked oligosaccharides for treatment of a wide variety of retinal diseases and disorders, as described below.

Methods of Treatment and Prevention Based on Retinal Glycan-Binding Proteins

One important aspect of the invention is a method for treating or preventing retinal diseases and disorders. The method includes administering to a subject in need thereof a therapeutically effective amount of a pharmaceutical composition comprising a multivalent glycan. As mentioned, it has been discovered that particular N-linked oligosaccharides can bind with very high affinity to a glycan-binding protein in the retina that appears to be expressed on the surfaces of Müller cells and is involved in facilitating the assembly of OS membranes in photoreceptors. Moreover, it has been found that binding of the N-linked oligosaccharides to the retinal glycan receptor can support OS membrane assembly even under abnormal conditions in which the photoreceptors are deprived of the support of the RPE cells. Accordingly, the invention provides a treatment method based on the observed desirable effects of binding of these glycans to the retinal glycan receptor.

More particularly, preferred or "permissive" glycans that can support this function in the retina are multivalent glycan ligands which are N-linked oligosaccharides having the general formula $(Gal-GlcNAc)_n-Man_3-GlcNAc_2$, where n is 1-4. In various embodiments, the compositions comprise a multivalent glycan that is a biantennary, triantennary or tetraantennary N-linked oligosaccharide, or any combination of these multivalent glycan ligands.

Particularly preferred multivalent glycans suitable for binding to a retinal glycan receptor in order to promote photoreceptor OS assembly include asialo, galactosylated, biantennary (NA2), and asialo, galactosylated, triantennary (NA3) oligosaccharides, which, as shown herein, bind to retinal glycan receptors on Miller cells with very high affinity. The chemical structures of several exemplary multivalent N-linked oligosaccharides in accordance with the invention are illustrated in FIGS. 11-13, and these compounds are further described infra.

The therapeutic multivalent glycans are preferably provided in the form of pharmaceutical compositions. Appropriate compositions are all compositions usually employed for topically or systemically administering drugs. The compositions comprise a pharmaceutically acceptable carrier which should be substantially inert, so as not to interact with the active component. "Pharmaceutically acceptable carriers" for therapeutic use are well known in the pharmaceutical arts, and are described, for example, in Remington's Pharmaceutical Sciences, Mack Publishing Co. (A. R. Gennaro, editor, 1985). Suitable inert carriers include water, alcohol polyethylene glycol, mineral oil or petroleum gel, propylene glycol and the like.

To prepare the pharmaceutical compositions of this invention, an effective amount of the particular multivalent glycan, e.g., an N-linked oligosaccharide as the active ingredient, is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration to the eye (intraocularly) percutaneously (or transdermally), to a mucosal surface, orally, rectally, or by parenteral injection. For example, in compositions suitable for intraocular administration, the carrier preferably comprises additives that do not introduce a significant deleterious effect on the eye. Suitable dosages and formulations of pharmaceutical compositions based on the active ingredients can be determined empirically, using methods well known in the art. Other compositions in accordance with the invention are formulated in a biodegradable matrix suitable for implantation into the eye, and for slow release of the therapeutic agent from the matrix. The use of such implantable matrices may be preferred in some instances, e.g., to obviate the need for repeated intraocular injections, as is the current standard of care for anti-VEGF drugs targeting the wet form of age-related macular degeneration.

In further embodiments, the invention provides kits for the treatment or prevention of eye diseases or disorders comprising one or more pharmaceutical compositions described herein and directions for use.

It is believed that the methods and compositions of the invention will be effective for the treatment of a wide variety of diseases and disorders having as their basis a biological function that is mediated by a glycan-binding protein such as the glycan receptor on Müller cells.

Preferred disorders are disorders of the eye, and particularly disorders affecting the retina, retinal pigmented epithelium (RPE), and/or choroid. A partial, non-limiting list of such conditions includes all forms of genetic-based retinal degenerations including retinitis pigmentosa of any form or etiology; Leber's congenital amaurosis; age-related macular degeneration (AMD); retinal detachments of any etiology; and infectious disorders. The disorders can include, e.g., viral infections such as CMV retinitis; systemic diseases that affect the eye such as diabetes and gyrate atrophy; hereditary forms of RPE dystrophy (e.g., Stargardt's disease/fundus flavimaculatus, Best disease/vitelliform dystrophy, congenital diffuse drusen/Doyne's honeycomb dystrophy, pattern dystrophies. Sorsby's macular dystrophy, choroideremia, and idiopathic bulls-eye maculopathies); and so-called "wet" and "dry" forms of age-related macular degeneration (AMD), as further discussed infra. Secondary RPE degeneration in retinitis pigmentosa conditions may also be a target of therapy. Diseases or disorders of non-genetic basis can further include toxic maculopathies, e.g., drug-induced maculopathies such as plaquenil toxicity.

In one particularly preferred embodiment, treatment methods in accordance with invention are thought to be potentially useful as therapeutic agents for the treatment of AMD. Presently. AMD is the most common ocular disease affecting the elderly in Western cultures. With the increasing longevity of the population over age 65, this disease is reaching epidemic proportions and will have a highly significant and increasing social and financial impact. As mentioned, the clinical presentation of AMD is typically characterized by one of two forms—either the atrophic (or "dry") form, which affects ~90% of those with AMD, or the exudative (or "wet") form of the disease. These conditions have been extensively described e.g., by Lewis (98). Briefly, the atrophic form of AMD presents with drusen formation, thickening of Bruch's membrane, subretinal pigmentary changes including lipofuscin deposition, and gradual visual loss. The hallmarks of the "wet" or exudative form of AMD, which can precipitate a medical emergency, are bleeding into the subretinal space due to growth of abnormal choroidal neovascular membranes ("CNV") which arise from the choroid, break through the RPE layer and bleed into the retina, undermining the normal RPE-photoreceptor relationship and causing RPE detachment, and formation of a scar of fibrous tissue. The devastating end result of CNV formation is degeneration of the photoreceptors in the macular region, the predominant site of formation of CNV.

Surgical excision of the neovascular membranes can be employed to remove the membrane from under the retina, but often this procedure also removes areas of RPE, which can cause further loss of function in the underlying photoreceptors. More recently, newer less invasive therapies have been developed that target the CNV in various ways. Several current treatments attack the CNV by reducing the expression of vascular endothelial growth factor (VEGF), a growth factor that promotes formation of the CNV. Current treatment methods for AMD have been recently described by Zarbin and Szirth (99).

AMD is a heterogeneous condition and its pathogenesis is known to be complex. A concerted worldwide research effort in recent years has resulted in certain genetic causes and/or predisposing factors for this disease to be elucidated. For example, recent studies have linked inflammation to the development and disease progression of AMD (100, 101). Based on the proposed role of the inflammatory process in AMD, a mouse model of AMD (i.e., the $Ccl2^{-/-}/Cx3cr1^{-/-}$ mouse) has been generated that develops retinal lesions that resemble some of the pathological features seen in AMD (102). As further described in Examples below, this and other animal models can be used to test the effectiveness of multivalent glycan-based therapeutic agents for the treatment of AMD and related conditions.

The therapeutic agents can be administered by any suitable method known in the art. In one embodiment of the method, the pharmaceutical composition comprising a multivalent glycan is administered to the eye of the subject. One suitable and well known method of administration is by intraocular injection. Alternatively, the composition may be incorporated into a biodegradable matrix suitable for implantation into the eye and for release of the composition into the interior of the eye, for example to the retina or adjacent RPE cells.

Method for Isolating a Glycan-Binding Protein

Using novel methods disclosed herein, a glycan-binding protein that binds with high affinity to preferred multivalent glycan ligands has been isolated and purified. To isolate glycan-binding proteins, such as those involved in promoting OS structural integrity in photoreceptors, the methods of the invention take advantage of the discovery by the inventor of a very high-affinity interaction between retinal glycan-binding proteins and certain glycan ligands.

The method includes at least one, and preferably all, of the following steps:

(a) contacting a retinal cell or a mixture of proteins or fragments thereof derived from a retinal cell with a glycan ligand under conditions that permit selective binding of said ligand to a glycan-binding protein or fragment thereof; and (b) isolating proteins that are selectively bound to the glycan ligand, thereby isolating a glycan-binding protein.

A preferred glycan ligand for isolating a glycan-binding protein is a multivalent N-linked oligosaccharide having the generic structure (Gal-GlcNAc)$_n$-Man$_3$-GlcNAc$_2$.

Various embodiments of multivalent glycan ligands useful in the invention can comprise linkages selected from fucosylation, N-acetylation, or sialylation. The sialic acid linkages can be Neu5Acα2-3 or Neu5Acα2-6. The galactose (Gal) residue linkage can be Galα1-4.

Figure 11A:
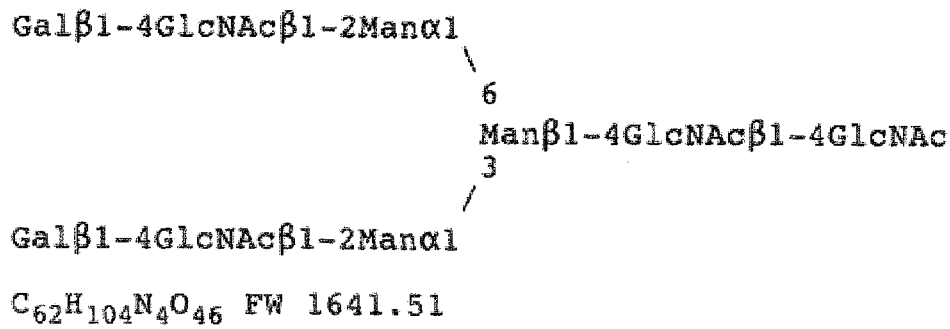
FIGS. 11A-C illustrate the chemical structures of several exemplary biantennary N-linked oligosaccharides that are useful for methods in accordance with the invention.

One family of multivalent glycan ligands having the above-described structure are biantennary N-linked oligosaccharides, wherein n consists of two (Gal-GlcNAc) moieties. One preferred biantennary N-linked oligosaccharide in accordance with the invention is an asialo, galactosylated, biantennary (NA2) oligosaccharide. The structure of an exemplary NA2 ligand is shown in FIG. 11A.

Figure 11B:
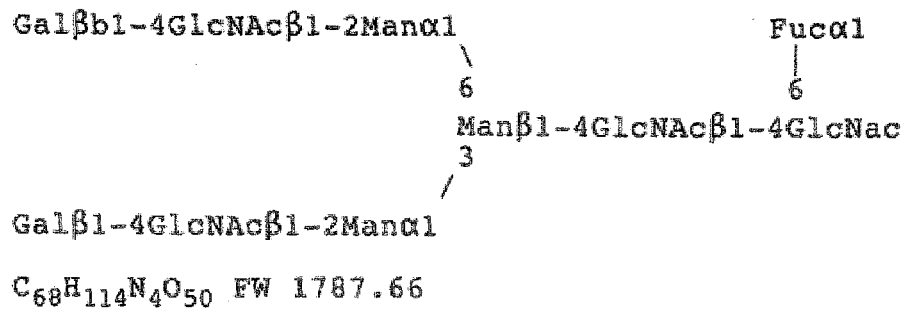

Another preferred biantennary N-linked oligosaccharide ligand of use in the invention is an asialo, galactosylated, fucosylated biantennary (NA2F) oligosaccharide. The structure of an exemplary ligand of this type is illustrated in FIG. 11B.

Figure 11C:
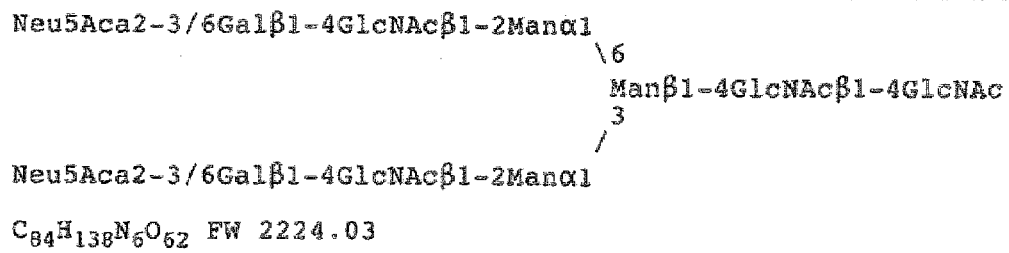

Yet a further useful biantennary N-linked oligosaccharide glycan ligand is a disialo, galactosylated, biantennary (A2) oligosaccharide, an example of which is shown in FIG. 11C.

Figure 12A:
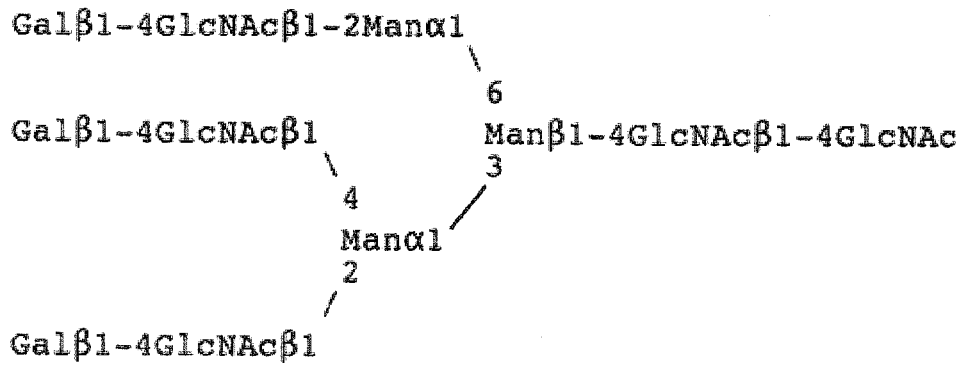
FIGS. 12A-B illustrate the structures of exemplary triantennary N-linked oligosaccharides, in accordance the invention.
Figure 12B:
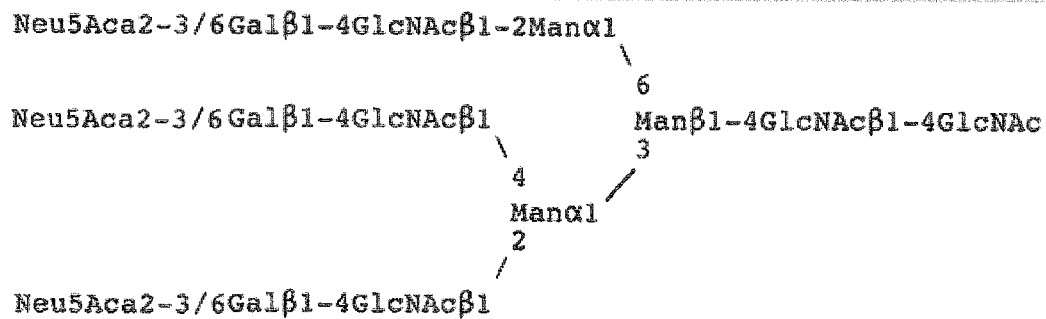
Figure 13:
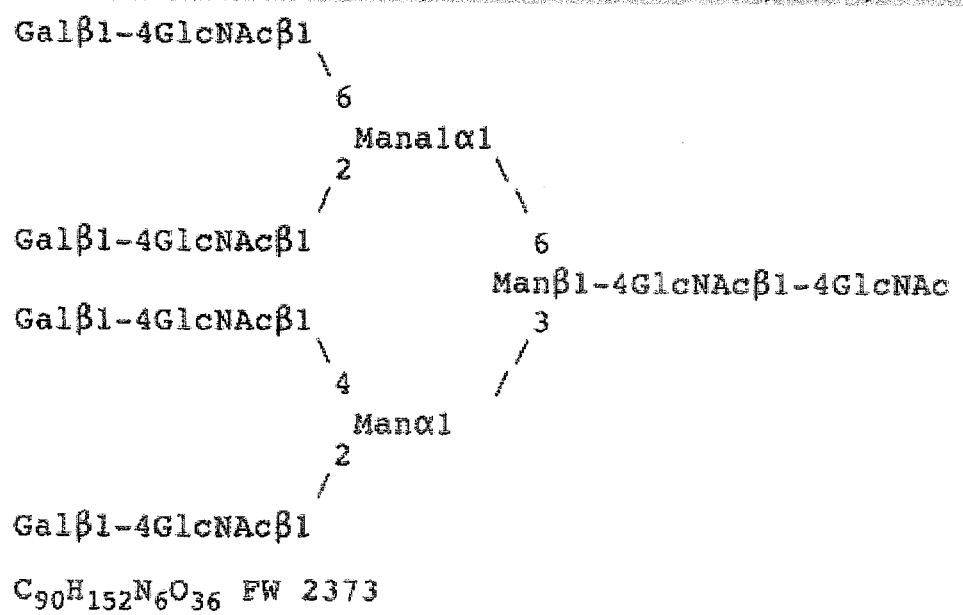
FIG. 13 shows the structure of NA4, an exemplary tetraantennary N-linked oligosaccharide.

Another family of multivalent glycan ligands suitable for isolating a glycan receptor includes triantennary N-linked oligosaccharides, or A3 family glycans, ((Gal-GlcNAc)$_3$), for which the structures of particular non-limiting examples are illustrated in FIGS. 12A-B.

One preferred triantennary N-linked glycan ligand of the A3 family is an asialo, galactosylated, triantennary (NA3) oligosaccharide. An exemplary NA3 ligand of this type is shown in FIG. 12A.

Another suitable triantennary glycan ligand is a trisialogalactosylated triantennary (A3) oligosaccharide. The structure of an exemplary A3 ligand of this class is shown in FIG. 12B. N-linked oligosaccharides of the A3 class occur in nature conjugated to a diverse group of glycoproteins (50). Such glycan ligands have been shown to be involved in tissue-targeting and cell activation in other tissues (see, for example, (51-53)).

Yet a further family of multivalent glycan ligands suitable for isolating a glycan receptor is that of the tetraantennary (A4) N-linked oligosaccharides, ((Gal-GlcNAc)$_4$). An exemplary A4 family glycan ligand is an asialo, galactosylated, tetraantennary (NA4) oligosaccharide, the structure of which is shown in FIG. 13. The above-described oligosaccharides are available from commercial sources. Those of skill in the art will recognize, however, that many modifications of the bi-, tri-, and tetravalent ligands could be synthesized and are within the scope of the invention.

In some preferred embodiments of the method, the glycan ligand is a non-metabolizable sugar.

In a particularly preferred method in accordance with the invention, a multivalent glycan ligand is useful to isolate a glycan-binding protein from the retina. In this application, a preferred ligand is a multivalent non-metabolizable glycan such as an asialo, galactosylated, biantennary (NA2) oligosaccharide, or an asialo, galactosylated, triantennary (NA3) oligosaccharide, as described above.

Details of methods useful for isolating a glycan-binding protein from a tissue or cell are further described in the following Examples. In several variations of the method of isolating a glycan-binding protein, recovery of the glycan-binding protein(s) is based on the use of a glycan ligand that is conjugated to an isolation tag. As used herein, the term "isolation tag" refers to a small molecule or nucleic acid/protein/glycoprotein sequence that is conjugated to the glycan ligand and can be used to assist in the isolation of a glycan-binding protein (receptor) that is bound to its respective ligand, by virtue of a very high affinity of the isolation tag for an "capture partner" molecule. Those of skill in the art will recognize that a glycan ligand can be conjugated with several different types of isolation tags that are suitable for coupling with appropriate isolation partner molecules and used to advantage in affinity purification schemes.

One well-known affinity purification scheme takes advantage of the high affinity binding that exists between avidin and streptavidin, e.g., using a biotin molecule as the isolation tag and an avidin/streptavidin molecule as the capture partner molecule. Biotin is a water-soluble B-complex vitamin comprising a ureido (tetrahydroimidizalone) ring fused with a tetrahydrothiophene ring. A valeric acid substituent is attached to one of the carbon atoms of the tetrahydrothiophene ring. Avidin is a glycoprotein that has a very strong affinity for biotin with a kD (dissociation constant) approximate to $10^{-15}$ M$^{-1}$, the highest known between any ligand and a protein. Avidin is a tetrameric protein attaching four molecules of biotin per tetramer. Streptavidin-containing compounds suitable, e.g., for use in chromatography are commonly used as affinity reagents for selective binding of biotin-conjugated molecules of interest. The term "streptavidin," as it is used herein, is meant to include any streptavidin molecule or fragment thereof or any protein that has an amino acid sequence that is at least 80, 90, 95, or 100% identical to a streptavidin molecule or fragment thereof (see, for example, Haeuptle et al. J. Biol. Chem. 258: 305, 1983). A preferred fragment of streptavidin is "core" streptavidin, which is a proteolytic cleavage product of streptavidin (Bayer et al. Biochem. J. 259: 369-376, 1989). By a "streptavidin-containing compound" is meant any compound that includes streptavidin covalently bound to another molecule. These compounds may, e.g., be conjugated to streptavidin through gene fusion technology or protein synthesis.

In one preferred embodiment of the method for isolating a retinal glycan-binding protein, biotin is used as an isolation tag that is conjugated to a glycan ligand. Methods are generally known in the art for conjugating a biotin molecule to a protein, or to a sugar such as a glycan. This process is commonly referred to as "biotinylation." The invention provides in one aspect reagents that are biotinylated glycans.

A preferred embodiment of a glycan in accordance with the invention that is conjugated to a biotin molecule is a biotinylated NA3 molecule. An important requirement for a biotinylated glycan that is useful for isolation of a glycan-binding protein is that the ligand binding sites of the glycan are preserved. To achieve this, the biotinylation procedure can be carried out under conditions that ensure that only the reducing end of the first carbon of the glycan chain is available to participate in the biotinylation reaction, thereby leaving the ligand binding sites free to interact with glycan ligand-binding proteins. Methods of making suitable biotinylated glycan ligands are further discussed infra, e.g., in Example 4.

In addition to their use as capture agents in affinity purification schemes, biotinylated glycans in accordance with the invention can be used to precisely localize the sites of binding of the biotinylated ligands to cells or subcellular targets of interest, e.g., by immunohistochemistry. As an example, see FIG. 5B, showing immunohistochemical staining of a retinal section following binding of a biotinylated NA3 ligand to ligand-binding proteins in the section. In the original color photo corresponding to this image, retinal nuclei are stained blue, and Muller cells are immunostained with an antibody against CRALBP, a Muller cell specific marker. The green staining in the image is due to immunostaining of the biotinylated NA3 ligand, using a primary antibody specific for biotin and a secondary antibody that emits a green fluorescent signal. As can be appreciated from the image in FIG. 5B, the ligand, bound to a retinal glycan-binding protein (receptor), appears to be localized to sites within Muller cells, the distribution of which is outlined by the red staining.

Another well-known affinity purification scheme takes advantage of the high affinity binding that exists between antigens and antibodies that selectively bind to the antigens. One version of the method of isolation of a retinal glycan-binding protein is based on antigen-antibody binding, in which the isolation tag conjugated to the glycan ligand is an antigen, and the capture partner molecule is an antibody directed against the antigen. In this isolation method, an immunoaffinity-based purification procedure is used to isolate glycan-binding proteins that are bound to the glycan ligand, by virtue of the binding of the antigen moiety of the glycan to the antibody capture molecule.

In one such isolation procedure based on immunoaffinity, the isolation tag is an aminoacridine molecule. In a particularly preferred embodiment of this method, the aminoacridine molecule is 3-(acetylamino)-6-aminoacridine (AA-Ac). The capture partner molecule in this method is an anti-acridine antibody that selectively binds to the aminoacridine molecule that comprises the isolation tag portion of the glycan ligand. A particular embodiment of a method for isolating retinal glycan-binding proteins based on immunoaffinity between AA-Ac and an antibody that specifically binds to AA-Ac is further described infra (see, e.g., Example 9).

Any suitable source of proteins can be used as the starting material for isolating a glycan-binding protein. A "tissue or cell" as used herein refers to any source of proteins obtainable from the body of an animal, such as an organ, particular body part, or naturally occurring or manmade cellular composition. For example, glycan-binding proteins have been identified in tissues such as the liver and cells such as those of the immune system such as macrophages and eosinophils (24-30). As one non-limiting example, tissue or cells that can be used as sources of glycan-binding proteins from the retina can be eye tissues, such as retinal tissue dissected free of one or more other tissues of the eye. As used herein, the term "retinal tissue or cell" refers to any cellular material derived from a retina obtained from any species. A retinal tissue or cell can include a whole retina, a portion of a retina, an isolated cell population enriched in one or more retinal cell types, including primary cultures, passaged cultures, and continuous cell lines, including immortal cell lines or a subcellular fraction isolated from a retina or retinal cell population. Additionally, another tissue or cell type other than one derived from the eye could be used as a source material for isolating a particular glycan-binding protein. This situation could arise, e.g., from an analysis of gene expression of an isolated retinal glycan-binding protein (e.g., by Northern blot or PCR analysis) indicating that whereas a retinal ligand-binding protein of interest is expressed in the retina, it is more abundantly expressed in another tissue of the body.

Isolated Retinal Glycan-Binding Proteins and Uses Thereof

Another aspect of the invention is an isolated glycan-binding protein. One preferred embodiment of this protein is an isolated glycan-binding protein that functions to promote the organization of outer segment (OS) membranes in photoreceptor cells of the retina.

Following the isolation of a glycan-binding protein to the level of purity of a single band on an electrophoresis gel, e.g., using novel protein isolation methods disclosed herein, the peptide or nucleic acid sequence of the isolated glycan-binding protein can be routinely obtained starting with the isolated protein species, using methods well known in the art and further described in Examples below.

As is well known, knowledge of the sequence of the glycan-binding protein provides all of the information necessary to develop a variety of research tools, screening assays and animal models for analysis of the glycan-binding proteins, as well as therapeutic molecules and methods for use in targeted approaches to diseases involving these glycan-binding proteins.

Based on the discovery and isolation of a novel glycan-binding protein in the retina as described herein, it is believed that knowledge of novel molecular players in the critically important pathway of photoreceptor OS assembly will lead rapidly to the development of new treatment modalities for degenerative retinal diseases and disorders including retinitis pigmentosa and age-related macular degeneration. As an example, knowledge of the nucleic acid sequences encoding the coding sequence, as well as genomic sequence associated with this protein, provides the basis for generating probes and primers that can be designed for various purposes. These reagents are useful, e.g. for gene screening, and detection of mRNA transcripts (for example by reverse transcriptase polymerase chain reaction (RT-PCR), such as by real-time quantitative PCR), based on the nucleic acid sequences of the gene, cDNA or portions thereof, as further described in Examples infra.

Specific agonists and antagonists of the gene encoding a glycan-binding protein, its mRNA, or protein can be designed, based on nucleic acid or amino acid sequences of the glycan-binding protein.

Using the polypeptide sequence of an isolated glycan-binding protein or an immunogenic portion thereof, antibodies can be produced using methods well known in the art, that specifically bind to amino acid sequences within the ligand-binding protein or polypeptide. Interacting molecules involved in the signal transduction pathway that is initiated upon binding of a glycan ligand to the receptor can be identified, for example, by using a molecular binding strategy such as a yeast two-hybrid system. Expression vectors that express the encoded cDNA can be designed and used, e.g., for gene therapy of mammalian retinal cells.

Another important utility of an isolated glycan-binding protein, and the corresponding cDNA sequence that encodes this protein, is in screening assays, including assays useful for identifying novel ligands that bind to these proteins. For example, in a cell-based assay system, an isolated glycan-binding protein can be expressed in a cell using recombinant DNA techniques well known in the art. Preferably, the expressed glycan-binding protein is expressed at the surface of the cell. Candidate ligands that can potentially bind to the cell surface protein are operatively linked to a detectable label (e.g. biotin) and can be identified by their detectable binding to the cell. These and other uses of the isolated glycan-binding proteins are further described in the Examples, infra.

Various forms of testing of an isolated retinal glycan-binding protein, e.g., a protein that is a putative cell surface receptor that mediates OS membrane assembly, can confirm the specificity and function of the protein. The affinity of the receptor for various glycan ligands can be demonstrated. The effect of specific inhibitors of the receptor on OS assembly can be conveniently carried out in an in vitro assay that supports OS assembly and growth under standardized conditions. One preferred assay system useful for this purpose utilizes the *Xenopus laevis* tadpole eye. Although it is a non-mammalian system, the intact *Xenopus* tadpole eye offers many advantages over mammalian systems including the following: it is a very well established and characterized model with a long history of use in the field of retinal cell biology and genetic studies; amphibian photoreceptors, under appropriate conditions, are capable of elaborating significant OS material in vitro, even in the absence of the RPE; the intact tadpole eye in the in vitro model approximates very closely the normal physiologic state; the simple culture conditions render the system easy to interpret and to manipulate in a tightly controlled fashion; and *Xenopus laevis* photoreceptors are very similar to humans photoreceptors, especially in regard to subcellular retinal architecture and protein expression.

In further embodiments, the assay can use a fragment of the glycan binding protein in screening assays to identify modulators of glycan-binding protein activity or expression.

Accordingly, the invention provides methods (also referred to herein as "screening assays") for identifying modulators. i.e., candidate or test compounds or agents (e.g., proteins, peptides, peptidomimetics, peptoids, small molecules or other drugs) which bind, have a stimulatory or inhibitory effect on the expression or activity of the glycan binding proteins identified by the methods of the invention.

In one embodiment, the invention provides assays for screening candidate or test compounds which bind to or modulate the activity or expression of a glycan-binding protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) J. Med. Chem. 37:2678-85); spatially addressable parallel solid phase or solution phase libraries; synthetic library methods requiring deconvolution: the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909-13; Erb et al. (1994) Proc. Natl. Acad. Sci. USA 91:11422-426; Zuckermann et al. (1994). J. Med. Chem. 37:2678-85; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233-51.

Libraries of compounds can be presented in solution (see, e.g., Houghten (1992) Biotechniques 13:412-421), or on beads (Lam (1991) Nature 354:82-84); on chips (Fodor (1993) Nature 364:555-556); on bacteria (Ladner, U.S. Pat. No. 5,223,409); on spores (Ladner U.S. Pat. No. '409); on plasmids (Cull et al. (1992) Proc Natl Acad Sci USA 89:1865-1869); or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; and Ladner, supra).

In one embodiment, a screening assay is a cell-based assay in which a cell which expresses an identified glycan-binding protein or a biologically active portion thereof is contacted with a test compound, and the ability of the test compound to modulate a glycan-binding protein or a biologically active portion thereof is determined. The cell, can be of mammalian origin, e.g., a cell isolated from the eye or the retina of a human.

The ability of the test compound to modulate a glycan-binding protein or a biologically active portion thereof binding to a compound can also be evaluated. This can be accomplished, for example, by coupling the compound with a radioisotope or enzymatic label such that binding of the compound is in a complex. Alternatively, a glycan-binding protein or a biologically active portion thereof could be coupled with a radioisotope or enzymatic label to monitor the ability of a test compound to modulate the glycan-binding protein substrate in a complex. For example, compounds can be labeled with $^{125}$I, $^{14}$C, $^{35}$S or $^{3}$H, either directly or indirectly, and the radioisotope detected by direct counting of radioemmission or by scintillation counting. Alternatively, compounds can be enzymatically labeled with, e.g., horseradish peroxidase, alkaline phosphatase, or luciferase, and the enzymatic label detected by determination of conversion of an appropriate substrate to product.

In yet another embodiment, a cell-free assay is provided in which a glycan-binding protein or a biologically active portion thereof is contacted with a test compound and the ability of the test compound to bind to the glycan-binding protein or biologically active portion thereof is evaluated. Preferred biologically active portions of the glycan-binding proteins to be used in assays of the present invention include fragments which have high surface probability scores.

Soluble and/or membrane-bound forms of identified proteins can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule can simply utilize the natural fluorescent energy of tryptophan residues. Labels are chosen that emit different wavelengths of light, such that the "acceptor"

molecule label can be differentiated from that of the "donor." Because the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET (also termed Fluorescence Resonance Energy Transfer ("FRET")) binding event can be conveniently measured through standard fluorometric detection means well known in the art (e.g., using a fluorimeter).

In another embodiment, determining the ability of the glycan-binding protein to bind to a target molecule can be accomplished using real-time Biomolecular Interaction Analysis (BIA) (see. e.g., Sjolander and Urbaniczky (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, cell-free assays can be conducted in a liquid phase. In such an assay, the reaction products are separated from unreacted components, by any of a number of standard techniques, including but not limited to: differential centrifugation (see, for example, Rivas and Minton (1993) Trends Biochem Sci 18:284-7); chromatography (gel filtration chromatography, ion-exchange chromatography); electrophoresis (see, e.g., Ausubel et al., eds. (1999) Current Protocols in Molecular Biology, J. Wiley, New York.); and immunoprecipitation (see, e.g., Ausubel et al., eds. (1999) Current Protocols in Molecular Biology, J. Wiley, New York). Such resins and chromatographic techniques are known to one skilled in the art (see, e.g., Heegaard (1998) J Mol Recognit 11:141-8; Hage and Tweed (1997) J Chromatogr B Biomed Sci Appl. 699:499-525). Further, fluorescence energy transfer can also be conveniently utilized, as described herein, to detect binding without further purification of the complex from solution.

EXAMPLES

The invention is further illustrated by the following non-limiting examples.

Example 1

In Vitro Assay System for Testing Ability of Compounds to Support Assembly of Photoreceptor Outer Segment (OS) Membranes This Example describes an exemplary assay system useful for testing the effect of candidate compounds on OS assembly in vitro.

We have used various oligosaccharides at concentrations ranging over four orders of magnitude to evaluate the ability of these oligosaccharides to support OS membrane assembly in RPE-deprived retina, using a *Xenopus laevis* system that allows for convenient analysis of OS membrane formation in vitro. In the RPE-deprived cultures, the RPE continues to be present as a cluster of cells at the ora serrata; however throughout the posterior pole and periphery of the retina, the RPE layer has been removed from its normal position adjacent to the photoreceptors.

Previous studies have shown that only lactose, galactose, and substituted forms of these permissive sugars permit OS to organize in the absence of the RPE. Other sugars, such as glucose, mannose, and fucose, fail to exert any organizational effect and thus have been termed "non-permissive" sugars (60, 61). It has been further demonstrated that lactose supports the expression of key photoreceptor and Müller cell proteins that are otherwise abnormally expressed in RPE-deprived retinas (62, 63).

FIGS. 1A-D illustrate representative results that are obtainable under the well-characterized experimental conditions provided by this assay system. Intact retinas were removed from stage 33/34 *Xenopus laevis* tadpoles and placed into culture in Niu-Twitty medium for three days as described above. Using this paradigm, all OS material is elaborated while in culture. Referring to FIG. 1A, in retinas maintained with an apposed RPE cell layer, the OS are tightly stacked, properly folded, and contain discs of equal diameter (arrows). This morphology is identical to that observed in tadpole retinas maturing in vivo. By contrast, in retinas deprived of the RPE but otherwise similarly maintained, photoreceptor OS membranes are markedly disorganized, with little evidence of normal disc stacking, as shown in FIG. 1B. Referring now to FIG. 1C, it is seen that the addition of $5 \times 10^{-3}$ M mannose does not favorably affect the folding of OS in RPE-deprived retinas (compare FIGS. 1B and 1C with FIG. 1A), whereas by contrast, the addition of $5 \times 10^{-3}$ M lactose supports the proper formation of nascent OS in the absence of the RPE (FIG. 1D).

Figure 2:
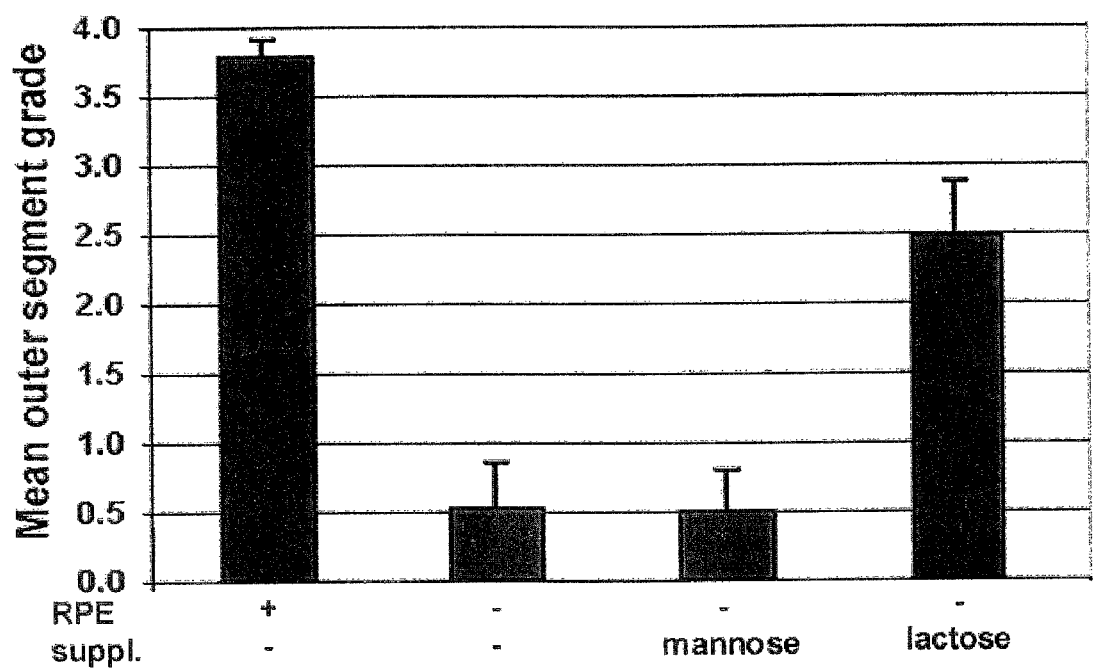
FIG. 2 is a graph showing a numerical grading system for evaluating OS assembly in vitro (mean±SEM), as applied to the assay system shown in FIG. 1.

Application of a quantitative grading scheme of OS morphology as described (67) reveals significant differences in the organization of OS under the above-mentioned culture conditions. By one-way ANOVA, the overall F-test for differences among the four groups is highly significant (FIG. 2; F=42.10; p value<0.0001). In retinas with an adherent RPE, the great majority of OS are highly structured, properly folded and contain discs of equal diameter. This corresponds to a grade of 3.71 (±0.09, SEM), in a scheme in which a grade of 4 represents the highest level (100%) of organization. In the absence of the RPE, the average grade of membrane organization decreases to, on average, less than 25% of the OS material being organized into stacked flattened membranous saccules. As expected, the addition of $5 \times 10^{-3}$ M mannose to the medium does not change the level of OS organization compared to RPE-deprived retinas (0.52±0.22, p=0.79), whereas exposure of the retinas to lactose (also $5 \times 10^{-3}$ M) results in an average organizational grade of 2.50±0.28, indicating that between 50 to 75% of the membranes are highly organized. Although the average value from lactose-supported retinas is lower than the control values from RPE-supported retinas (p=0.0009), it is significantly greater than the organizational grade of both RPE-deprived retinas and those exposed to mannose (FIG. 2, p<0.0001).

Example 2

Support of OS Assembly is Mediated by Non-Metabolizable Sugars

This Example demonstrates that the ability of certain "permissive" sugars to support photoreceptor OS assembly can occur via a saturable, non-metabolic mechanism, consistent with the interaction of the sugar with a cell surface receptor.

The results presented in Example 1 above show that lactose and galactose, which are examples of "permissive" glycans, are able to support photoreceptor OS membrane assembly to a level that is significantly greater than in its absence. Because lactose and galactose are sugars, however, it is possible that they may exert their OS organizational effect through a metabolizable property, e.g., by merely providing an energy source to the cells (such as by feeding into the Krebs' cycle), or by permitting glycosylation of some essential proteins, or both.

Figure 3A:
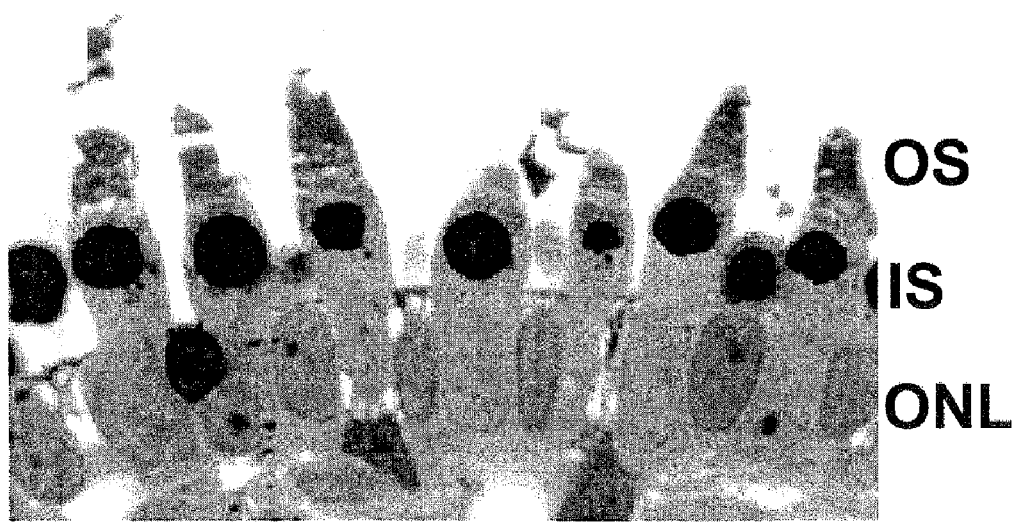
FIG. 3A is a photograph and FIG. 3B is a graph showing that isopropyl beta-D-thiogalactopyranoside (IPTG), a non-metabolizable form of galactose, can support proper OS assembly in RPE-deprived retinas, comparable to the effect mediated by lactose.

To separate out the metabolizable properties of permissive sugars from properties unrelated to sugar metabolism, intact RPE-deprived retinas from *Xenopus* tadpoles were exposed to isopropyl beta-D-thiogalactopyranoside (IPTG), a non-metabolizable form of galactose, at concentrations ranging over five orders of magnitude (68), and subsequently graded for organization of OS. Referring to FIG. 3A, the results revealed a step-wise improvement in photoreceptor OS organization with increasing concentrations of IPTG, up to a maximum effect (i.e., at $5\times10^{-5}$ M), after which the ability of IPTG to support proper OS assembly was reduced.

Figure 3B:
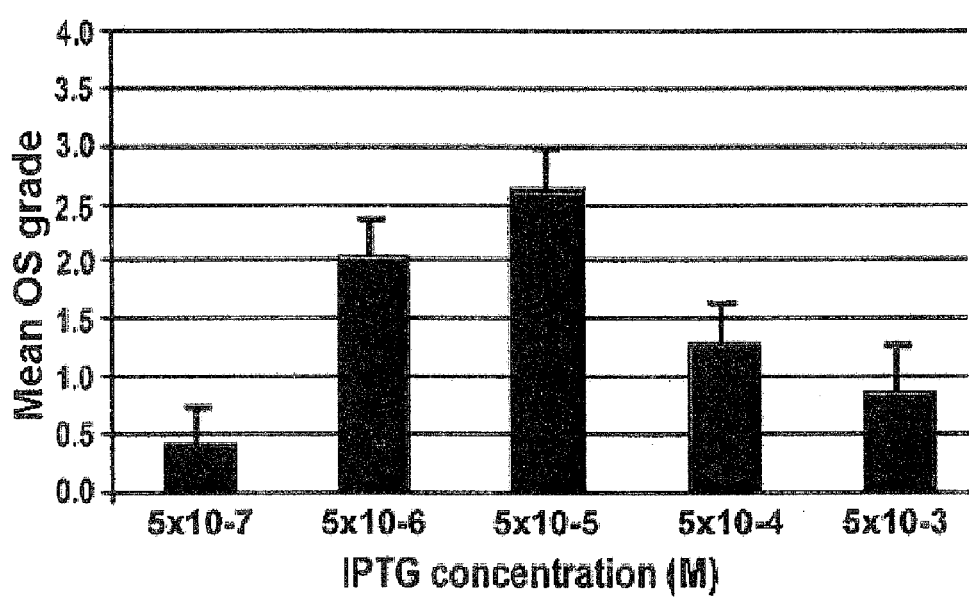

FIG. 3B shows the quantitative grading of OS elaborated in the presence of various concentrations of IPTG (mean±SEM). By one-way ANOVA, the overall F test for differences among the four groups is highly significant (F=6.15, p value=0.0002). The maximum response was obtained with $5\times10^{-5}$ M, with an average grade of 2.61±0.37. This value is significantly greater than that for RPE-deprived eyes, but it is not different from that of lactose-exposed retinas (compare to FIG. 2). Thus, the use of IPTG as a substitute for the metabolizable permissive sugars permits one to separate out the non-metabolic aspects of permissive glycan function. Of particular note, the observed morphological effect on OS assembly in RPE-deprived retinas is not only comparable to that described for lactose (19, 60-62), but it can be achieved at 100-fold lower concentration.

Example 3

Support of OS Assembly by Permissive Sugars is Reversible

This Example describes results of experiments demonstrating that the support of OS assembly by permissive sugars occurs by a mechanism that is reversible.

Figure 4A:
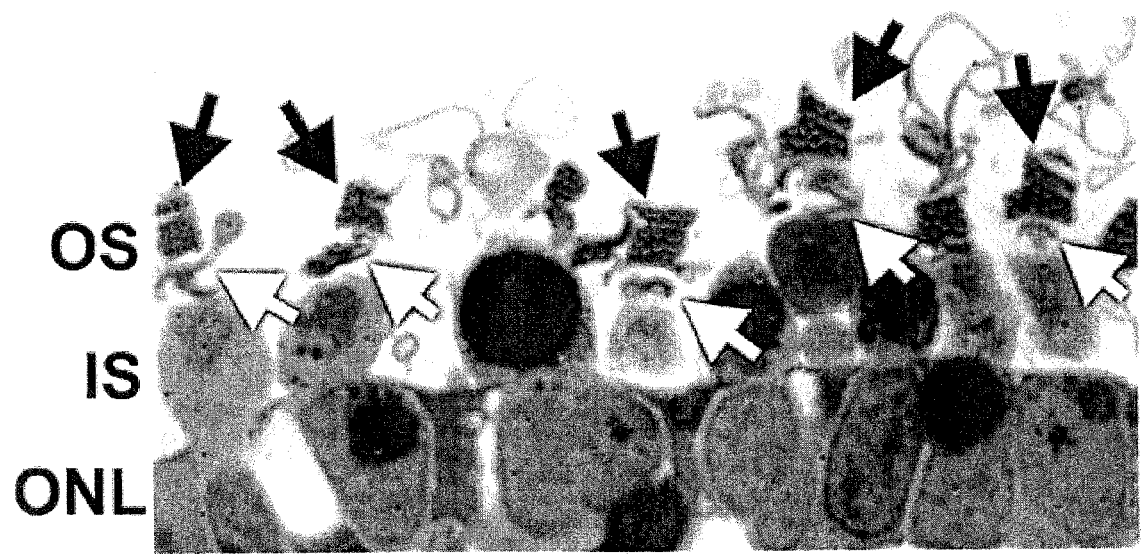
FIG. 4A is a black and white reproduction of a color photograph of an autoradiogram of RPE-deprived retina exposed to IPTG and $^3$H-leucine for two days, followed by non-supplemented (non-radioactive) medium for two days. Pseudo-colored dots (red color in original) indicate the location of silver grains corresponding to $^3$H-leucine which has been incorporated into newly-synthesized proteins that are present in the OS membranes indicated by the black arrowheads.

RPE-deprived retinas were exposed to permissive sugars at optimal concentrations (i.e., $5\times10^{-3}$ M lactose and $5\times10^{-5}$ M IPTG), supplemented with $^3$H-leucine for a period of two days, followed by an additional two days in non-supplemented medium. FIG. 4A illustrates an example of an RPE-deprived retina that was exposed to IPTG using the above-described culture paradigm. The photograph shown in FIG. 4A is a composite of a brightfield image overlaid with a darkfield image that was pseudo-colored (in this case, red). In the majority of the photoreceptors, the OS membranes that are most displaced from the inner segment portion of the photoreceptor, and therefore were assembled during the early part of the culture paradigm during the period of exposure to IPTG and $^3$H-leucine, were properly assembled (indicated by dark arrows in FIG. 4A).

Figure 4B:
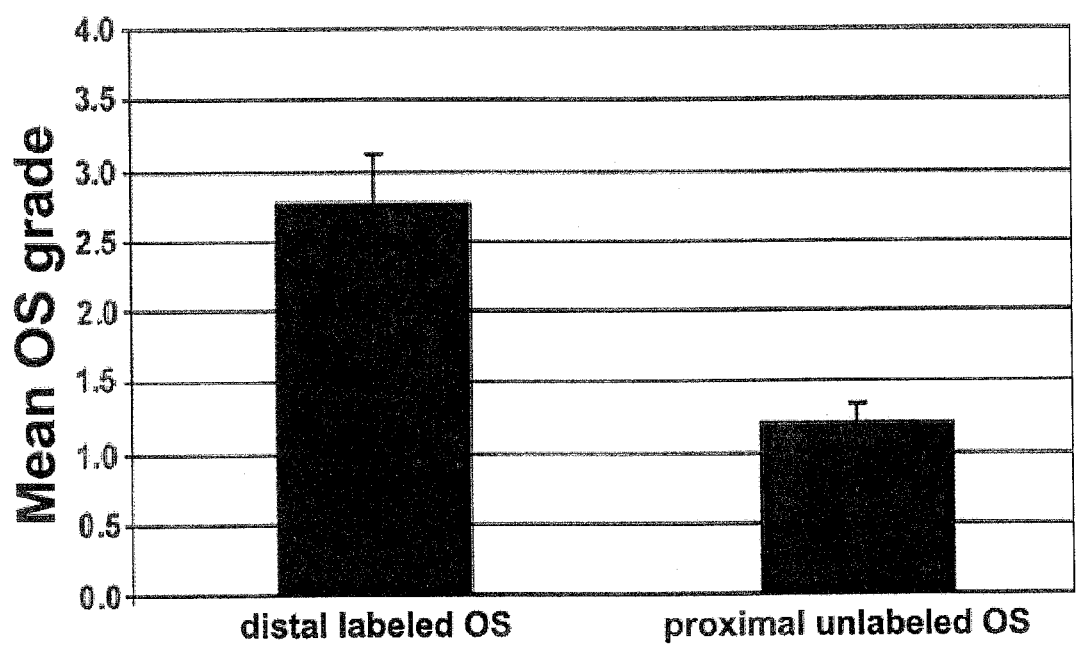
FIG. 4B is a graph showing grading of OS organization (mean±SEM) during the early and later portions of the assay depicted in FIG. 4A.

Referring to FIG. 4B, the average grade of these membranes was about 2.88±0.37. By contrast, membranes that are in closer proximity to the inner segments, and therefore were assembled during the later stage of the experiment when the eyes were exposed to non-supplemented medium, are significantly more disorganized (indicated by light arrows in FIG. 4A). These membranes had an average grade of 1.21±0.31, a value that is significantly less than that of OS membranes assembled during the early part of the experiment (FIG. 4B, p=0.0014). These results demonstrate that proper OS assembly is directly responsive to stimulation by IPTG, and that removal of the sugar results in disruption of the sugar-mediated OS membrane assembly. These results provide strong evidence for reversibility of the observed organizational effect on OS membranes that is mediated by permissive sugars (64).

Example 4

Identification of High Affinity Multivalent Oligosaccharide Ligands that Bind to Retinal Glycan Receptor The above-described properties of saturability and reversibility of support of OS assembly by permissive glycans provide evidence for the presence of a glycan receptor in the retina, the activation of which permits the proper folding and assembly of nascent OS membranes. This Example describes the discovery of a very high affinity of the receptor for multivalent ligands in the form of complex oligosaccharides.

The *Xenopus* culture paradigm was used to test the ability of complex oligosaccharides with varying valency (i.e., varying number of terminal galactose residues) to support OS assembly. NA2 (asialo, galactosylated, biantennary) and NA3 (asialo, galactosylated, triantennary) NA2 and NA3 were applied to isolated RPE-deprived *Xenopus* tadpole eyes as described above, at concentrations ranging from $5\times10^{-6}$ to $5\times10^{-11}$ M.

Figure 5A:
FIG. 5A is a photograph showing robust support of OS assembly (arrows) in RPE-deprived retina exposed to a low concentration of multivalent glycan ligand NA3 ($5\times10^{-10}$M), according to an embodiment of the invention.
Figure 5B:
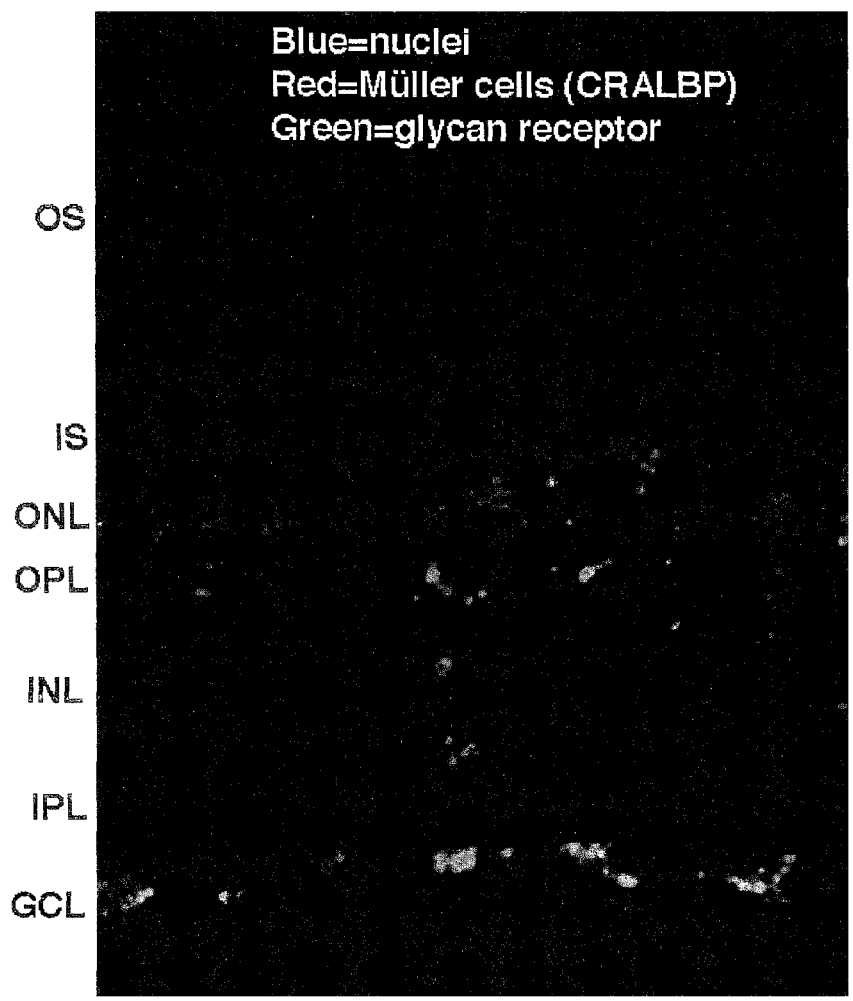
FIG. 5B is a black and white reproduction of a color photograph of an immunostained retinal section showing binding of biotinylated NA3 glycan ligand to putative glycan receptor binding sites (green fluorescence in original; seen here as light spots in a punctuate pattern overlying Muller cells, which are immunostained with a cell specific marker (CRALBP, red fluorescence in original). Cell nuclei are counterstained with DAPI (blue fluorescence in original).

Referring to FIG. 5A, the results indicated that NA2 and NA3 optimally support OS assembly at concentrations of $5\times10^{-9}$ and $5\times10^{-10}$ M, respectively. These concentrations indicate that the putative retinal glycan receptor has a very high affinity for these multivalent ligands. Furthermore, the affinity of the receptor for these ligands significantly increased with increased valency of the ligands (NA2 has two terminal galactose residues whereas NA3 has three terminal galactose residues), indicating that these sugars, and particularly N3, could be useful in designing a strategy for isolating the retinal glycan receptor.

Taking advantage of the demonstrated strong affinity of NA3 for the glycan receptor, we investigated which retinal cell type(s) are able to bind NA3. Embryonic *Xenopus laevis* retinas were exposed to two experimental conditions: (1) biotinylated-NA3; and (2) biotinylated-NA3 with a molar excess of IPTG as a competitive sugar, to eliminate non-specific interactions of NA3 with retinal proteins. After exposure to the sugars followed by immunostaining using a mouse anti-biotin primary antibody and a chicken anti-mouse secondary antibody coupled to Alexa fluor 594 using standard protocols, eyes were bisected and viewed using a confocal microscope.

Figure 5C:
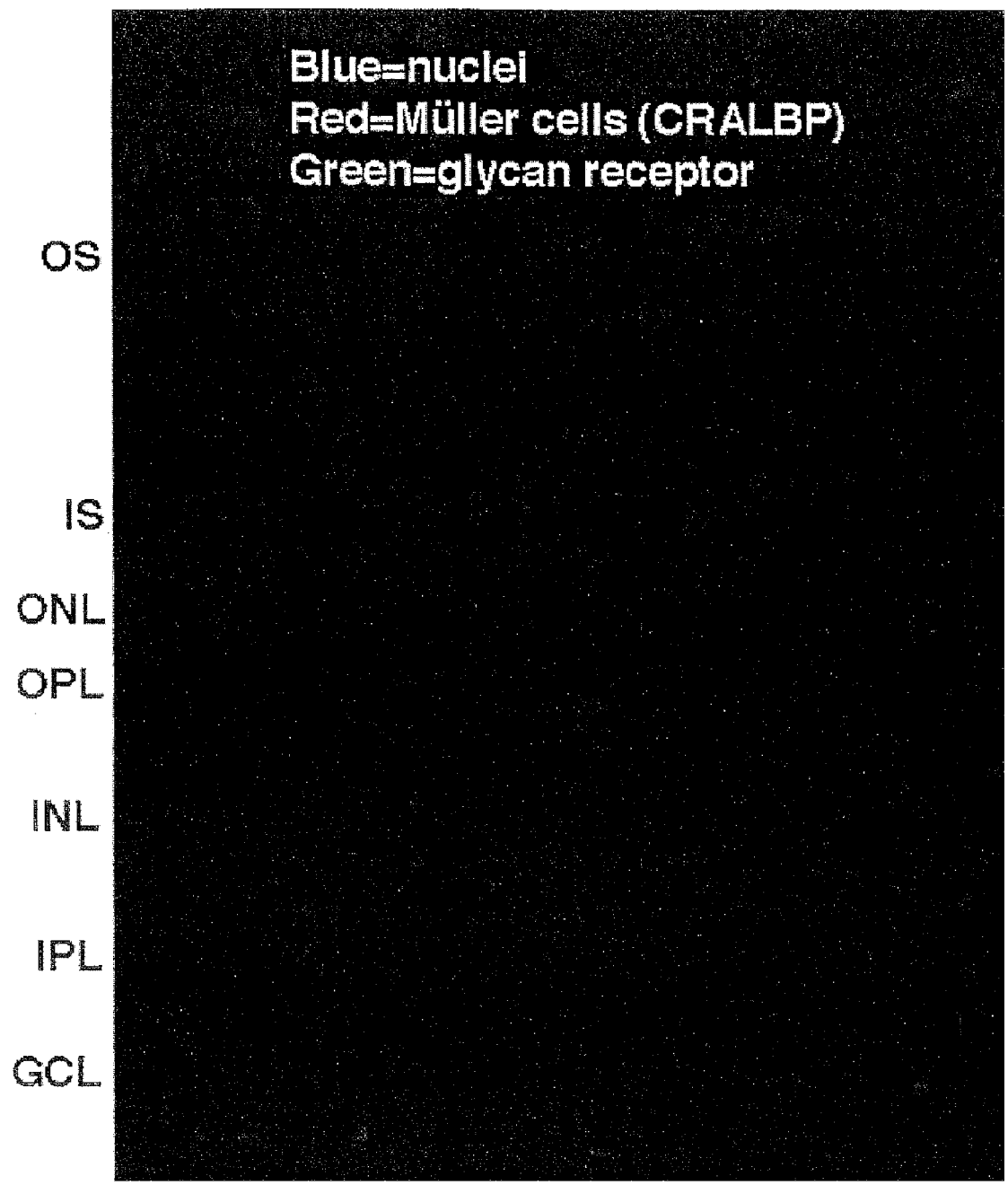
FIG. 5C is a photograph as in FIG. 5B showing absence of the punctuate binding pattern of NA3 over Muller cells, in a control sample incubated with an excess of a competitive sugar, IPTG.

Referring to FIG. 5B, eyes exposed to biotinylated NA3 showed heavy labeling throughout the retina. The distribution of immunoreactivity associated with NA3 binding strongly suggested that NA3 binds to Müller cells, as the observed pattern of labeling is virtually identical to that of GFAP, glutamine synthetase and cellular retinaldehde binding protein, all well known markers specific for Müller cells (63). The NA3 ligand did not bind to any portion of photoreceptors. Labeling seen in the area of photoreceptor nuclei in the outer nuclear layer (ONL) is likely in Müller cell processes that surround photoreceptor nuclei in this region of the retina. The observed labeling pattern was present in all four of four retinas that were evaluated in this study. By contrast, the control retinas showed no labeling (FIG. 5C).

Example 5

Purification of Retinal Glycan Receptor Using Biotinylated NA3

This Example describes a novel protocol for isolating and purifying a retinal glycan receptor utilizing biotinylated-NA3 as a high affinity receptor-binding ligand.

RPE-deprived *Xenopus laevis* tadpole eyes were cultured in medium containing biotinylated-NA3 at $5 \times 10^{-7}$ M for 3 hrs, to allow NA3 to bind to the glycan receptor. Two control conditions were used: one set of control eyes was exposed to biotinylated-NA3 plus a molar excess of unlabeled IPTG as a competitive permissive sugar. Additional control retinas were exposed to culture media alone without any permissive glycan.

Five hundred eyes were harvested after culture and total protein extracts were run over an avidin column (ProFound™ Pull-Down Biotinylated Protein:Protein Interaction Kit; Pierce) to capture all biotinylated molecules, along with any proteins to which the biotinylated molecules are bound with high affinity. The appropriate controls were applied to the avidin column according to the manufacturer's protocols.

Figure 6:
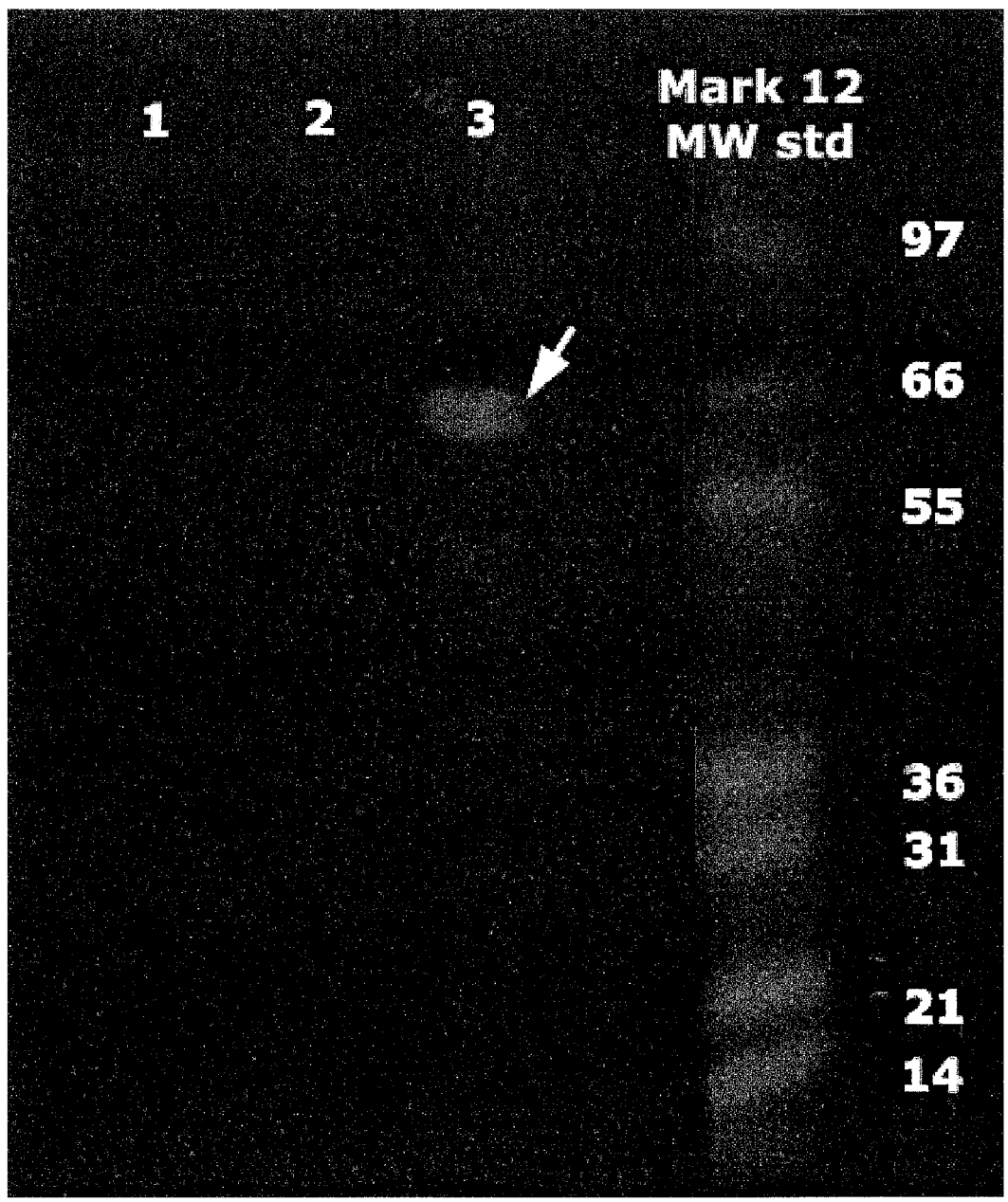
FIG. 6 is a photograph of Sypro ruby-stained gel of samples of retinal extract eluted from an avidin column during purification of retinal glycan-binding proteins, in accordance with an embodiment of the invention. Eyes were exposed to: culture media only (lane 1), biotinylated-NA3 plus excess IPTG (lane 2), or biotinylated-NA3 only (lane 3).

The protein(s) coupled to the biotinylated-NA3 were eluted from the avidin column and run on a one-dimensional SDS-PAGE gel under reducing conditions. A typical result, shown in FIG. 6, revealed a single protein band of ~63 kD eluted from the column to which retinal samples exposed to biotinylated-NA3 were applied (lane 3). This band was not present in avidin columns loaded with control extracts of retinas exposed to biotinylated-NA3 plus competitive sugar (FIG. 6, lane 2) or culture media alone (FIG. 6, lane 1). This result demonstrates the high affinity of the NA3 ligand for a glycan receptor in the retina. Under the disclosed experimental conditions, we were able to obtain a single protein band that was not present in either of the control conditions, indicating that this procedure is an effective approach to isolating a glycan receptor from the retina (FIG. 6, lane 3).

The results shown in FIG. 6 demonstrate that the above-described protocol is effective for isolating a single protein band from a retinal extract using a biotinylated-NA3 ligand, when the ligand is applied to intact RPE-deprived retinas. We have determined that an important step is to apply the biotinylated-NA3 probe to the intact retinas, so that it preferentially binds to proteins associated with the cell surface membrane, such as the glycan receptor, and to extracellular proteins. By contrast, when total retinal proteins are extracted prior to exposure to the NA3 probe, five proteins ($MW_r$ 202 kD, 140 kD, 63 kD, 55 kD and 31 kD) are isolated from the columns, rather than the single species obtained using the protocol described above.

Further detailed description of the isolation, purification and identification procedures are as follows:

1. Acquisition of stage 33/34 *Xenopus laevis* retinal tissue. Details of this methodology have been previously published (see, e.g., 57, 59-62). *Xenopus laevis* embryos are obtained through induced breeding of adult frogs by injection of human chorionic gonadotropin. Embryos are staged by external morphologic criteria as described by Nieuwkoop and Faber (72). Eye rudiments are removed from stage 33/34 tadpoles. At this stage, the sclera-choroid layers have not yet enveloped the eye rudiments; therefore, the RPE is the outermost cell layer. We have demonstrated that eyes removed from this stage of tadpole are very responsive to permissive glycans (19, 23, 57, 59-61), thereby indicating that the receptor is expressed and active. Lighting conditions are preferably cyclic (12 hr light: 12 hr dark) and provided by incandescent illumination equivalent to approximately 200-250 lux/m² at the level of the cultures (62).

Figure 7A:
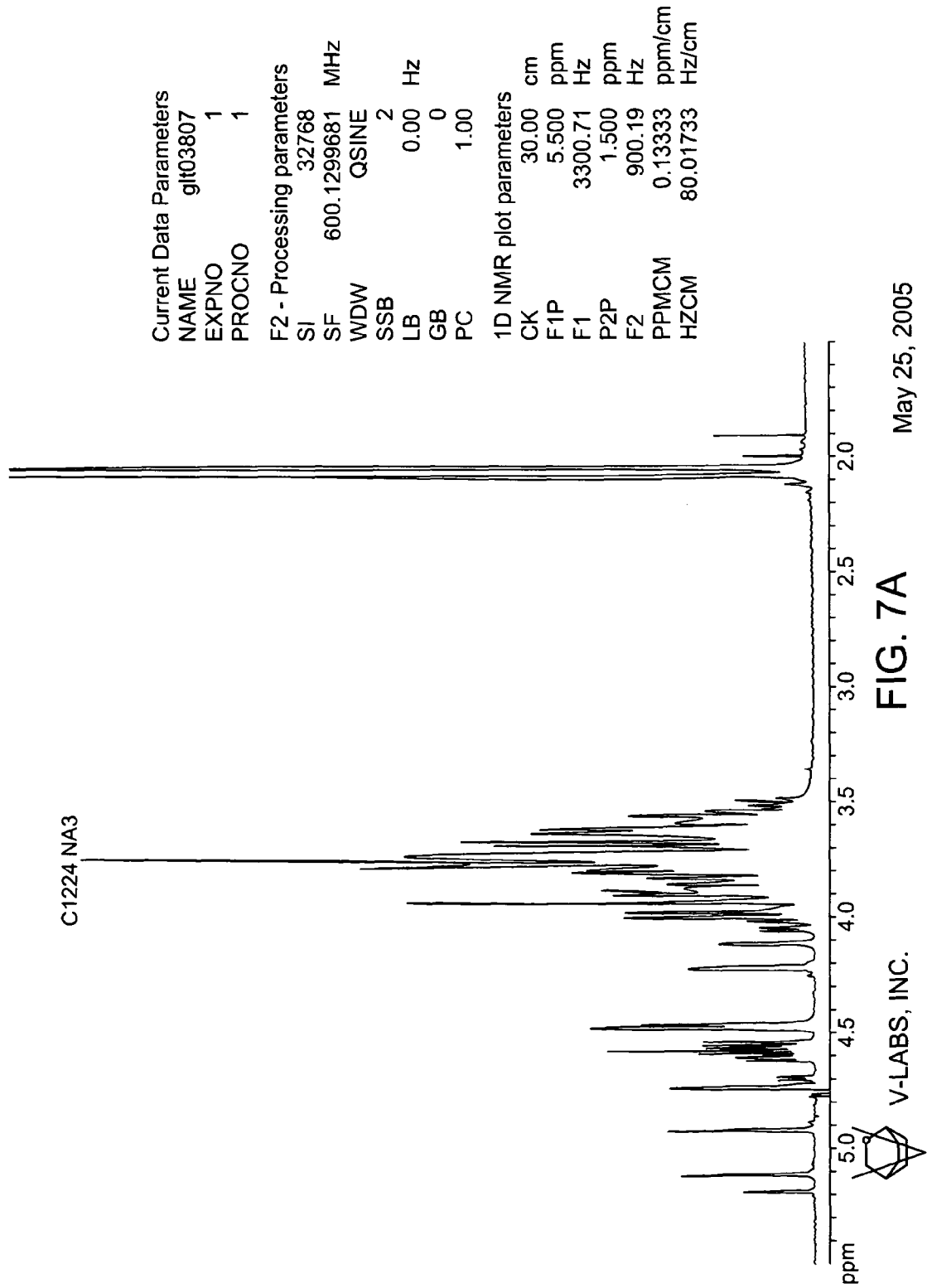
FIG. 7A is a graph showing mass spectrometric analysis and FIG. 7B is a graph showing HPLC analysis, both graphs documenting the purity of NA3 multivalent oligosaccharide useful in the isolation of a retinal glycan receptor, according to an embodiment of the invention.
Figure 7B:
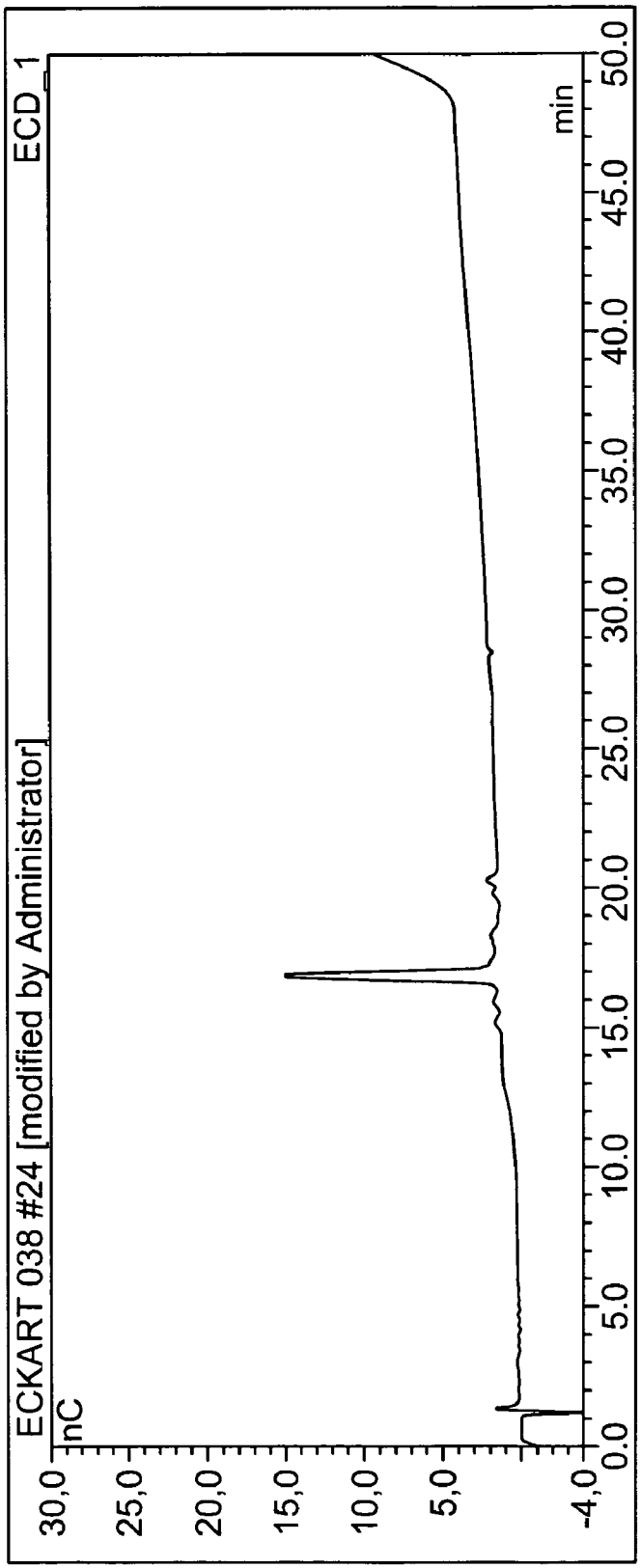

2. Generation of biotinylated-NA3 ligand. Asialo, galactosylated, triantennary NA3 (V-Labs; >95% pure as verified by mass spectrometry and HPLC, as shown in FIGS. 7A-B respectively), are biotinylated with the EZ-Link Biotin-LC-Hydrazide kit (Pierce) following the manufacture's protocol, with the modification that the NA3 is not oxidized prior to biotinylation to preserve the ligand binding sites of the glycan. Therefore, only the reducing end of C1 of the glycan chain is available to participate in the biotinylation reaction. Following labeling, the mixture is passed through a Sephadex G15 column (Amersham) according to the manufacturer's instructions to separate unbound biotin from the biotinylated-NA3. The Sephadex G15 material has a fractionation range of 1500 and is therefore able to readily separate the biotinylated-NA3 (MW 2377.52) from the free biotin-LC-hydrazide (MW 371.5). Nine ml of Niu-Twitty buffer is slowly applied to the column to elute the components. Fractions are collected as 18 fractions of 500 μl each and tested separately for the presence of biotin and glycan.

Figure 8:
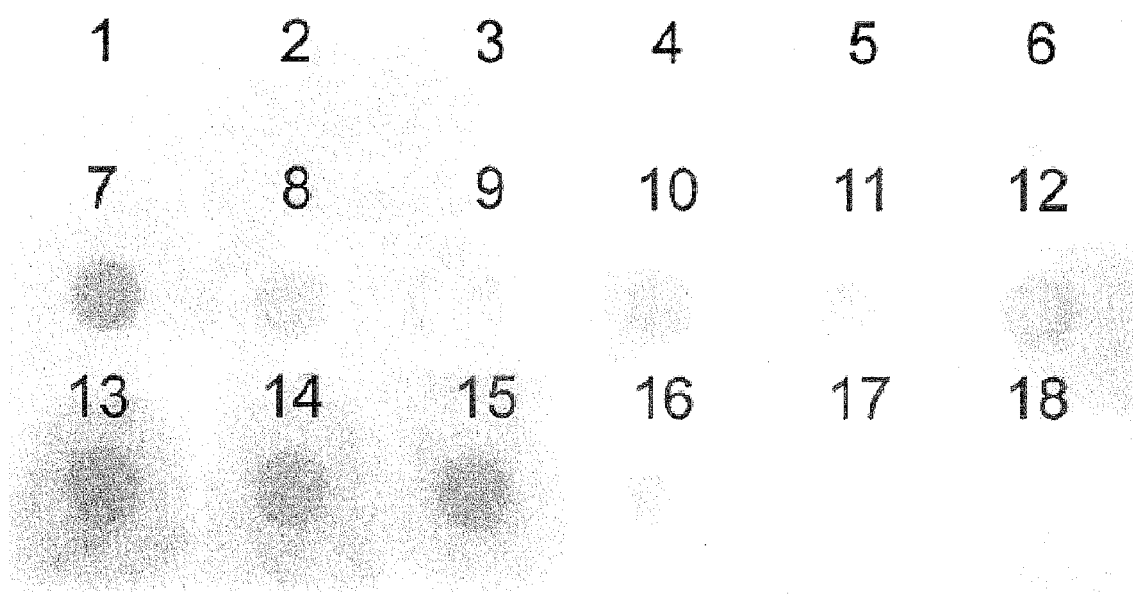
FIG. 8 is a photograph showing a biotin dot blot probed with streptavidin-AP, documenting the relative abundance of biotin in fractions eluted from an avidin column used to purify retinal glycan-binding proteins, in accordance with an embodiment of the invention.
Figure 9A:
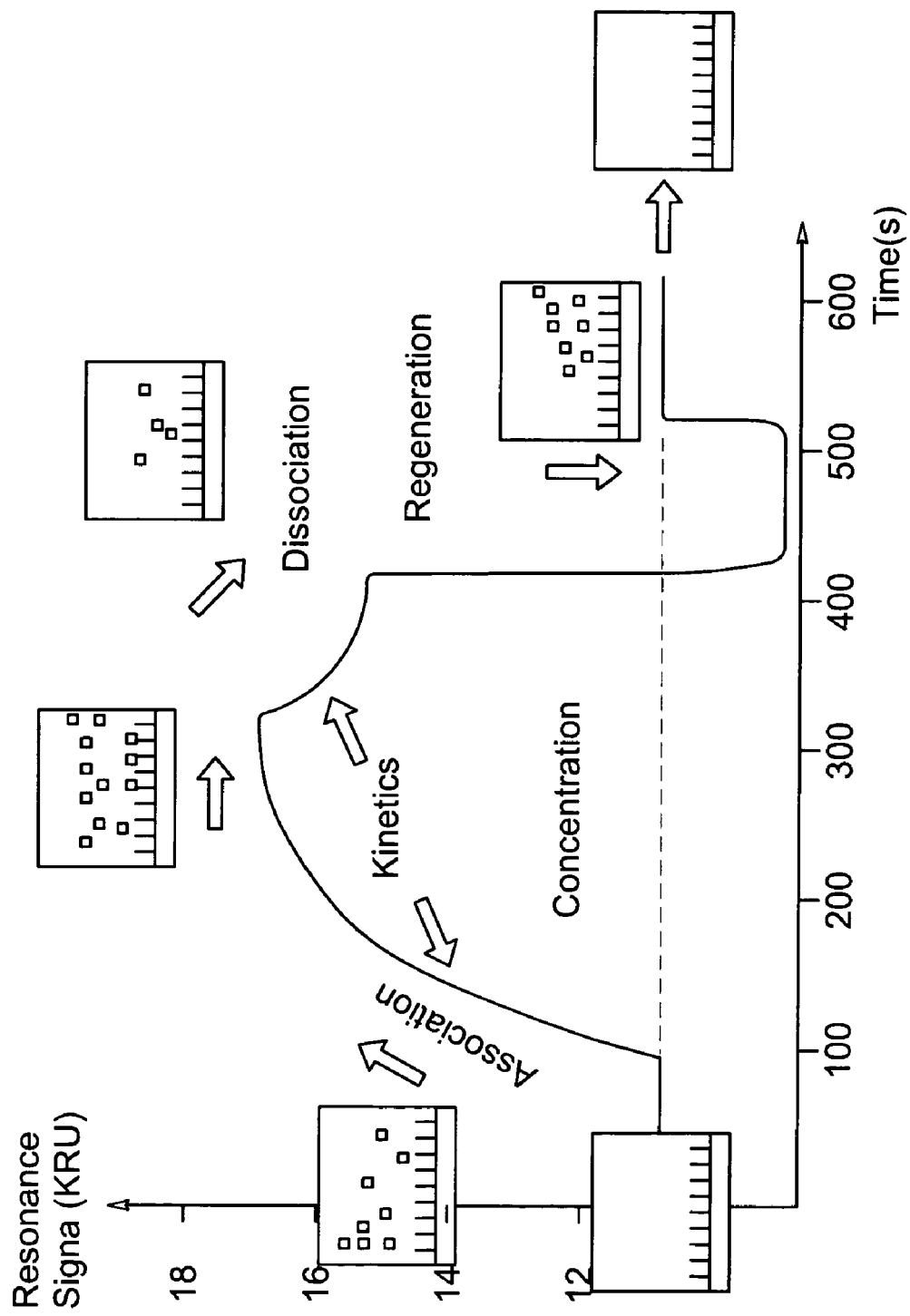
FIG. 9A is a schematic diagram illustrating a typical sensorgram generated by Surface Plasmon Resonance (SPR), a technique that may be used to assess the nature of interactions between retinal glycan receptors and their ligands, according to an embodiment of the invention.
Figure 9B:
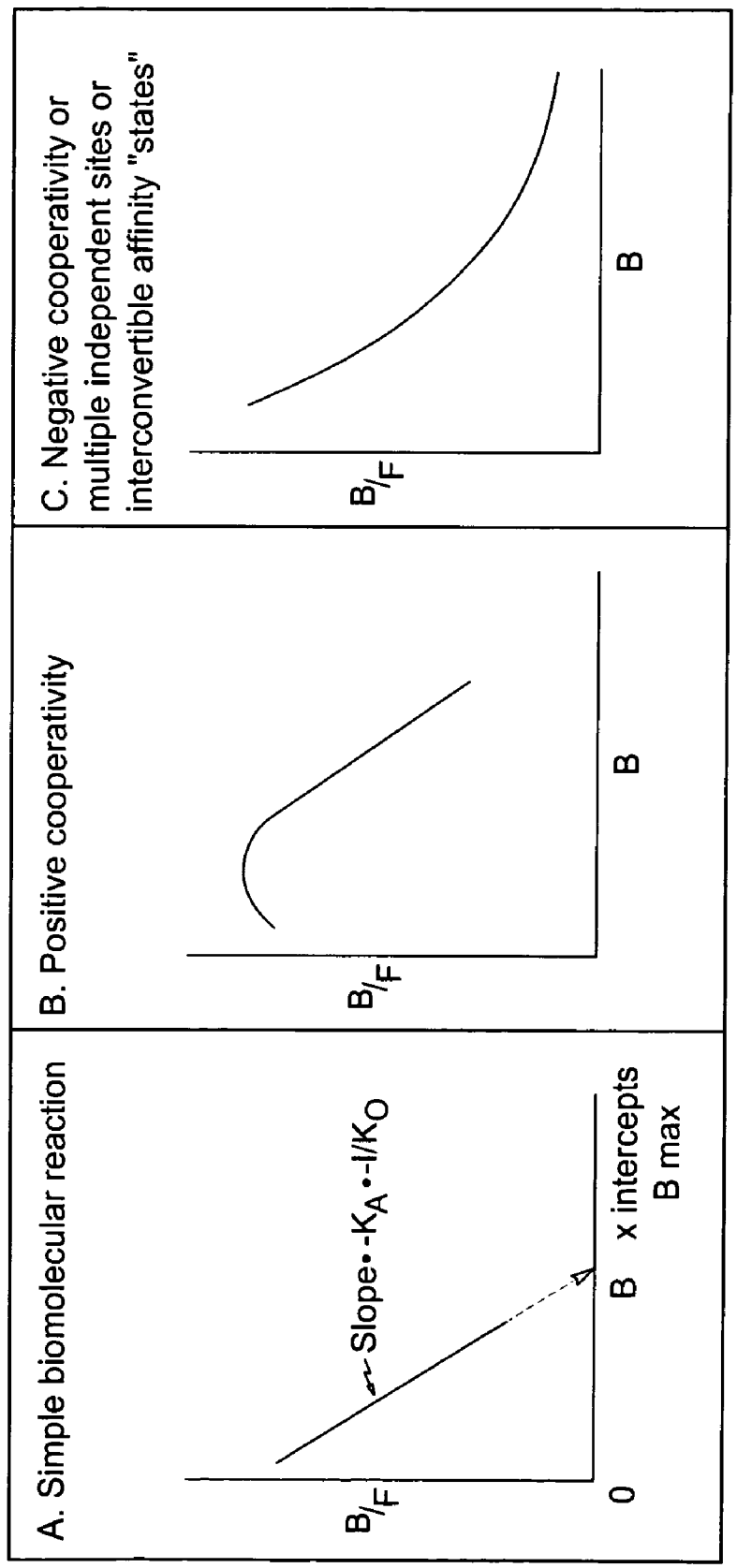
FIG. 9B is three graphs showing on the left, middle, and right, respectively, three types of spectrograms generated under conditions involving: a simple biomolecular reaction; positive cooperativity; and negative cooperativity.

To test for the presence of biotin, 20 μl from each collection tube is applied to Hybond-P membrane using a dot-blot apparatus (BioRad). The membrane is incubated in streptavidin alkaline phosphatase followed by rinses in 50 mM Tris-HCl, 154 mM NaCl, 0.05% Tween-20, pH 7.4, (TTBS). ECF™ (GE Biosystems), a substrate that makes a fluorescent product when reacted with alkaline phosphatase is applied to the membrane, after which time the membrane is scanned on a Typhoon 9400 Imaging Device at 560 nm using ImageQuant software (V. 3). Samples that contain biotinylated-NA3 and free biotin appear positive on the blot, as shown in FIG. 8. The earliest samples that are biotin-positive contain biotinylated-NA3 because they are eluted from the Sephadex G15 column first due to its molecular weight. The later biotin-positive samples contain free NA3, which elutes from the column in the latter fractions because it is retained on the column.

To determine the presence and concentration of glycans in the eluted fractions, the protocol of Saha et al. (73) may be used. Briefly, 0.1 ml of each fraction is placed in a separate 7 ml vial. A 0.1 ml volume of glycan standards ($10^{-3}$ to $10^{-7}$ M galactose) is run in parallel and water is used as a blank. A volume of 0.1 ml of 5% phenol is added and mixed. A 0.5 ml volume of concentrated sulfuric acid is added and the solution is allowed to reach its maximum reaction temperature. After cooling, the absorbance is read at 480 nm on a Spectronic Unicam spectrophotometer and the concentration of the NA3 sample is determined from the standard curve. Adjustments are made in the concentration to account for the single galactose molecule in the standard vs. the three terminal galactose residues present on NA3. The samples that contain both biotin and glycan contain the biotinylated-NA3. As an example, in the data shown in Table 1 infra, fractions 5-7 would be combined and used as the biotinylated-NA3 probe.

3. Receptor-ligand binding and purification of the glycan receptor. Biotinylated-NA3 ($10^{-7}$ M) is diluted in Niu-Twitty medium. Three sets of RPE-deprived *Xenopus laevis* tadpole retinas are cultured as follows: under one experimental condition (i.e., $10^{-7}$ M biotinylated-NA3) and two control conditions (i.e. $10^{-7}$ M NA3+$10^{-5}$ M IPTG as a competitive glycan, and Niu-Twitty medium alone). Each set comprises several pools of 1000 retinas, each from stage 33/34 *Xenopus* tadpoles. Retinas are harvested after three hours of culture.

Total protein is extracted using 1% C7BzO (Calbiochem), due to its superior ability to solubilize membrane proteins. As an additional control, the solubilized proteins are first precleared on a D-mannose agarose column (Sigma). The flow-through is then used to purify the glycan receptor. The Pro-Found™ Pull-Down Biotinylated Protein:Protein Interaction Kit (Pierce) is used to isolate and purify the protein that binds to the biotinylated-NA3 according to manufacturer's instructions. Eluates are applied to 4-12% SDS-PAGE gradient gels and run under both reducing and non-reducing conditions, followed by silver or Sypro ruby staining according to manufacturer's protocols. A representative run under reducing conditions is shown in FIG. 6.

TABLE 1

Concentrations of NA3 in 18 fractions collected from a G15 column

| Fraction from G15 column | Absorbance at 480 nm | Approx. Conc $10^{-5}$ M |
|---|---|---|
| 1 | 0.008 | Under range |
| 2 | 0.011 | 0.06 |
| 3 | 0.022 | 0.09 |
| 4 | 0.030 | 0.11 |
| 5 | 0.067 | 2.2 |
| 6 | 0.075 | 2.4 |
| 7 | 0.065 | 2.1 |
| 8 | 0.025 | 0.10 |
| 9 | 0.022 | 0.09 |
| 10 | 0.017 | 0.07 |
| 11 | 0.019 | 0.08 |
| 12 | 0.018 | 0.08 |
| 13 | 0.016 | 0.07 |
| 14 | 0.014 | 0.07 |
| 15 | 0.012 | 0.06 |
| 16 | 0.016 | 0.07 |
| 17 | 0.008 | Under range |
| 18 | 0.005 | Under range |

4. In-gel digestion of proteins and liquid chromatography/mass spectrometric (i.e., LC/MS/MS) analysis of tryptic peptides. The band identified as the permissive glycan receptor is excised and subjected to tryptic digestion followed by LC/MS/MS analysis of the tryptic peptides using the protocol of Giorgianni et al. (74). Briefly, the purified glycan receptor is mixed with sequencing grade trypsin (10 µg, Promega). Digestion is carried out overnight (37° C.), and stopped by the addition of acetic acid (30 µl; final pH 3.0). The tryptic peptides are manually loaded onto a capillary C18 PicoFrit column (New Objective) packed with 9-10 cm of C18 silica-based reversed-phase packing material (5 µm, 200A MAGIC C18) from Michrom Bioresources. Column packing is carried out under nitrogen gas pressure (400-500 psi) with a homemade pressure-vessel. Samples are analyzed with a gradient-elution program that includes a 5-min initial isocratic elution with 0% B; a linear gradient 0-70% B in 60 min (1.05% acetonitrile min$^{-1}$); a 5-min isocratic elution with 70% B; and a linear gradient 70-0% B in 10 min, where A=water-0.1% formic acid, B=90% acetonitrile-10% water-0.1% formic acid.

Peptides are eluted at a 100 nL/min flow rate, and introduced online into a nanoESI-quadrupole ion-trap MS (LCQ$^{Deca}$, ThermoFinnigan). The instrument is set to execute one MS scan followed by a zoom scan of the most intense peptide signal, and by an MS/MS scan of each one of the four most intense peaks from the MS scan. The MS/MS data (.dta files) are searched against the vertebrate protein subset obtained from the SwissPROT protein sequence database, with the search engine SEQUEST (75) that is part of the LCQ$^{Deca}$ software package.

5. Scale-up procedures. As demonstrated above using 500 eyes, the above-described methodology for purifying a retinal glycan receptor can isolate a single protein band under reducing conditions. Typically, a minimum of about 5 ng of purified protein is required to characterize a protein. 1-1.5 ng of protein can be isolated from 500 *Xenopus* eyes as described, which represents the lowest limit of detection for MS/MS characterization of a protein. Therefore, scaling up the procedure as described above by five-fold allows for sufficient protein to be purified. Those of skill in the art can isolate ~1000 tadpole eyes in one day; therefore this number of eyes can be easily obtained and is not limiting.

An alternative approach to increasing the yield of protein available for MS analysis is to bypass running the purified receptor on an SDS-PAGE gel, and to proceed directly to LC/MS/MS of the protein. By doing so, the protein yield is improved and protein is not lost during the extraction procedure from the gel. Yet a further alternative to facilitate isolating the receptor is to first isolate membrane proteins, e.g., using a Mem-PER Eukaryotic Membrane Protein Extraction Kit (Pierce), and then apply only the membrane proteins to the ProFound™ Pull-Down Biotinylated Protein:Protein Interaction Kit (Pierce), as described above.

6. Molecular identification of the isolated receptor protein. The purified permissive glycan receptor is isolated in sufficient quantity to obtain an accurate identification of the protein, e.g., using tryptic digestion and mass spectrometric analyses as described above. The purified receptor is identified using LC-mass spectrometric methods.

Another variation of a procedure for isolation and purification of the glycan receptor may be carried out essentially as follows:

a. NA3 is tagged with fluorescein hydrazide at the reducing end of the glycan.
b. NA3-fluorescein is incubated with intact retinas to allow ligand to bind to receptor.
c. The receptor is crosslinked to the ligand with THPP (β-[Tris(hydroxymethyl)phosphino]propionic acid
d. The membrane is isolated and membrane-associated proteins are separated from soluble proteins using ultracentrifugation.
e. The membrane and membrane-associated proteins are solubilized with n-dodecyl beta-D-maltoside (DDM) detergent.
f. The solubilzed proteins are applied to an anti-FITC pull down column.
g. The column is washed to remove non-specifically bound proteins.
h. The glycan receptor is eluted with glycine (pH 2.0).
i. The eluant is neutralized with Tris (pH 8.5).
j. The isolated protein is submitted for MS analysis, as described.

Efforts are underway to sequence the entire genome of *Xenopus tropicalis* (<www.sanger.ac.uk>, <www.jgi.doe.gov>, and <www.tigr.org>), as well as *Xenopus laevis* (<www.xgc.nci.nih.gov>) itself. Thus, the identification of the glycan receptor should be greatly facilitated. Moreover, various BLAST engines are available to compare the sequence information that we obtain from our study with that in the *Xenopus* databases (see for example the *Xenopus* Gene Collection at http://xgc.nci.nih.gov).

Additionally, TIGR (www.tigr.org) hosts EGO (Eukaryotic Gene Orthologs), which is a database for orthologous genes in eukaryotes. As stated by TIGR. "EGO is generated by pair-wise comparison between the Tentative Consensus (TC) sequences that comprise the TIGR Gene Indices from individual organisms. The reciprocal pairs of the best match are clustered into individual groups and multiple sequence alignments are displayed for each group."

The EGO database is "blasted" with the protein sequences that obtained via the MS/MS data, allowing for comparison of orthologous gene products from other species. If the protein is novel or the identity of the protein remains ambiguous, MALDI-ToF-ToF MS can be performed to determine the amino acid sequence of a purified glycan receptor protein.

Example 6

Quantitative Kinetic Measurements of Interactions Between NA3 and Glycan Receptors This Example describes methods of analyzing quantitative kinetic measurements of the interactions between a glycan ligand such as NA3 and a retinal glycan receptor by Surface Plasmon Resonance (SRS) technology. Such analysis is useful to elucidate details of biospecific ligand-receptor interactions, e.g., to determine whether the receptor-ligand interaction comprises a simple bimolecular reaction, positive cooperativity, or negative cooperativity.

Surface Plasmon Resonance (SPR). SPR is a technology that allows for real-time detection and monitoring of biomolecular binding events. This methodology is based on the use of a sensor chip to which an analyte is bound. The interacting partner is presented to the analyte in a liquid phase that is allowed to flow over the chip. In studies described herein, the ligand is immobilized and the receptor is allowed to flow over the chip. Interactions between the analyte and interacting partner are detected as changes in mass in the aqueous layer close to the sensor chip. As molecules bind, the mass increases, and likewise, when they dissociate, the mass decreases. This change in mass is detected as a change in refractive index of incident light that illuminates the sensor chip.

A system suitable for SPR analysis is produced by Biacore (GE Healthcare). The Biacore system generates a sensorgram, which is a graphical representation of the association and dissociation of the receptor and ligand and is based upon the change in refractive index at the surface of the sensor chip (FIG. 9A). Biacore and the related BIAEvaluation software are powerful tools that allow for identifying binding partners for target molecules, and also provide quantitative data on the specificity of the interaction, the concentration of binding partner, the rates of association and dissociation of the receptor-ligand interaction and also the strength or affinity of the interaction (50).

The data describing the interactions between the receptor and ligand can be fit to various models, to determine whether the interaction follows first or higher order kinetics, and to determine the stoichiometry of the biospecific interaction. For example, a simple bimolecular reaction with one molecule of ligand binding to one molecule of receptor would lead to a linear Scatchard plot (illustrated in the left panel of FIG. 9B). A concave downward curve as seen in the middle panel of FIG. 9B suggests that the receptor population to which the ligand is binding exhibits positive cooperativity, meaning that the receptor affinity for the ligand increases with increasing occupancy of the receptor. An upward concave curve as seen in the right panel of FIG. 9B can result from multiple independent sites with dissimilar yet constant affinities for the ligand; multiple affinity sites for a receptor; or negative cooperativity (51).

SPR technology has been shown to be suitable for analyzing and evaluating the interactions between lectins and their carbohydrate ligands. For example, SPR has been used to demonstrate that *Sophora japonica* agglutinin binds to immobilized lactose in a dose-dependent manner (53). And to determine the specificity of the lectins *Maackia amurensis* agglutinin (MAA) and *Sambucus nigra* agglutinin (SNA) for sialic acid residues (54). Specifically, it was demonstrated that MAA bound only to carbohydrates containing Neu5Ac or Neu4,5$Ac_2$ (α2-3) linked to galactose, whereas SNA only bound to Neu5Ac or Neu4,5$Ac_2$ (α2-6) linked to galactose. Using immobilized asialofetuin, the lectin, *Ricinus communis* agglutinin (RCA) was shown to have a lower association-rate constant than *Datura stramonium* lectin (DSA), whereas its dissociation-rate constant was higher; thus the affinity constant was significantly higher for DSA (55).

Further detailed description of the use of SPR analysis of retinal glycan receptor interaction with glycan ligands is provided as follows:

1. SPR Analysis of Receptor-Ligand Interactions.

These studies are conducted, e.g., using a Biacore 3000 instrument. All procedures are performed using the standard methodologies. A suitable ligand such as NA3 is immobilized to the carboxymethylated dextran layer on a CM5 sensor chip using an aldehyde coupling protocol without prior oxidation. Alternatively, a SA Sensor Chip, which is designed to capture biotinylated molecules, is used along with biotinylated NA3 ligand. The flow rate during the immobilization step is about 5 μl/min. Reagents are injected in the following order: 0.4M 1-ethyl-3-(3-dimethylaminopropyl)-carbodiimide in water; 0.1M N-hydroxysuccinimide in water; 5 mM carboxyhydrazine in water; 1M ethanolamine; NA3; 0.1M sodium cyanoborohydride in 0.1M sodium acetate pH 4. An average of 1000 arbitrary response units of NA3 is immobilized in each flow cell. Mock or negative control surfaces are generated by replacing NA3 with running buffer.

A solution containing a putative receptor as part of a membrane preparation is injected over the sensor chip surface. The mass accumulation of the receptor on the surface of the chip is recorded in arbitrary units that are directly proportional to mass. Kinetic assays are carried out at 25° C. at a flow rate of 5 μl/min. Data collection rate is set to about 10 Hz. Different dilutions of each membrane preparation (described infra) are injected over the sensor chip containing NA3 for 300 seconds, followed by a 300 second long injection of buffer. Regeneration of the sensor chip is accomplished by two 5 μl pulse injections of 120 mM HCl solution. Sensorgrams, as shown schematically in FIG. 9A, are subjected to curve fitting with numerical integration methods using BIAEvaluation (version 4.1) software (Biacore).

2. Cell Membrane Preparations.

Preferably, several different membrane preparations are utilized in these studies, including cell-free membrane preparations obtained from stage 34/35 *Xenopus* tadpole eyes (obtained as 10 described above), adult *Xenopus* retinas, the A6 *Xenopus* kidney cell line (i.e. ATCC number CCL-102 (66)), a mouse cone-like photoreceptor cell line (67), a human rod-like photoreceptor cell line (i.e, ATCC number HTB-18 (68, 69)) and a rat Müller cell line (70). Cell lines A6 and HTB-18 are commercially available from American Type Culture Collection (ATCC). Membranes from cell types not expected to express a retinal glycan receptor (such as photoreceptors, kidney cells, etc.) provide one useful control for the specificity of the procedure.

As an alternative to cell lines, primary retinal cells can be used as a source of cell membranes. Primary retinal cells should have the majority (if not the entire) complement of cell membrane proteins expressed on their membranes. Dissociated primary cells from *Xenopus* retinas can be sorted using Fluorescence Activated Cell Sorting (FACS), e.g., after differentially labeling photoreceptors and Müller cells with distinct fluorescent tags such as FITC and Texas Red.

Cells are maintained using standard culture protocols in 75-mm² flasks containing the appropriate culture medium for each cell line: A6 kidney cells—75% NCTC 109 medium, 15% dH$_2$O, 10% fetal bovine serum (FBS); 661W cone-like photoreceptors—Dulbecco's modified essential medium (DMEM) containing 10% FBS and 1% penicillin/streptomycin (67); HTB-18 rod-like photoreceptors—RPMI 1640 with 2 mM glutamine, 1.5 g/L NaHCO$_3$, 4/5 g/L glucose, 10 mM HEPES. 1.0 mM Na pyruvate, 10% FBS; rMC-1 Müller cells—DMEM with 10% FBS and glutamine (70).

Cellular fractionation is performed using standard protocols (71). Briefly, retinas or cells are homogenized in a Dounce homogenizer (20 strokes, pestle A) in ice-cold HEPES buffer containing protease inhibitors. The homogenate is centrifuged with a J2-21 high-speed centrifuge (Beckman Instruments) at 1,000×g for 10 minutes to pellet the nuclear fraction. The supernatant is then centrifuged at 10,000×g for 20 minutes to pellet the mitochondrial fraction. The post-mitochondrial supernatant is further centrifuged at 100,000×g for 2 hours. The pellet, which contains the membranous fraction, is diluted in HEPES buffer and utilized to collect kinetic data describing the interactions between the putative glycan receptor and the NA3 ligand.

To verify that a retinal glycan receptor is present in a particular membrane preparation, the experiment is preferably repeated with the addition of an antibody against the candidate receptor protein, if available. The antibody, which should block any interactions of the receptor with the NA3 ligand, is incubated with the membrane preparation prior to its application to the SPR sensor chip.

A sensorgram indicating an interaction of the ligand (such as NA3) with any of the membranous preparations is interpreted as quantitative kinetic data describing the interaction of a glycan receptor with the ligand. Exposure of the membrane preparations to the anti-glycan receptor antibody prior to application to the sensor chip that results in elimination of interaction of the receptor with the ligand indicates that (1) the receptor is present in the membrane preparation and (2) the receptor is the candidate protein recognized by the antibody.

Comparison of sensorgrams obtained using the various membrane preparations, along with the appropriate negative controls, permits analysis of differential expression of the receptor. For example, the inclusion of the A6 *Xenopus* kidney cell line allows for determination of the presence of the receptor in one type of non-retinal *Xenopus* tissue. The inclusion of membranes from adult *Xenopus* retinas allows for inquiry into the temporal expression of the receptor during development and adulthood, and determination of whether expression of the receptor is downregulated after morphogenesis of the photoreceptors is complete, for example. Furthermore, by testing membrane preparations of various retinal cell types from different species it is possible to ascertain whether the receptor is present in the membranes from one or more retinal cell types; and to isolate homologous receptors from retinal cells of various species.

As previously discussed, the SPR method provides quantitative information regarding the specificity of binding, the active concentration of receptor in the sample as well as the kinetics and affinity of the interaction. Advantageously, because SPR technology allows for capture of the receptor-binding partner from a complex mixture, prior purification of the receptor is not required. By comparing the results obtained with different cell-free membrane preparations, it is possible to demonstrate the existence of a particular glycan receptor (or absence thereof) in retinas from different ages of *Xenopus* (tadpole vs. adult), different tissues (e.g., *Xenopus* retina vs. kidney), as well as different cell types (e.g., rod vs. cone vs. Müller cell) and species (e.g., *Xenopus* vs. rat vs. mouse vs. human). Because of the exquisite specificity of the glycan receptor for the NA3 ligand, only those cells expressing the receptor can interact with the biosensor chip to which NA3 is coupled. These data can also be compared to the results obtained by methods for localizing the receptor within the retina, as discussed in Example 7, infra.

Example 7

Localization of Retinal Glycan Receptor

This Example describes methods for localizing glycan receptors in the retina, and results of experiments performed to test whether Müller cells of the retina are implicated in the observed support of OS assembly by permissive sugars.

Alpha-aminoadipic acid (α-AAA), an analog of L-glutamate that accumulates at toxic levels within Müller cells, is known to cause selective, reversible cytotoxicity in Müller and brain glial cells in vivo (69-71) and in vitro (72, 73). We have previously demonstrated that inhibition of Müller cell metabolism has direct consequences on photoreceptor assembly (22). Exposure of RPE-supported *Xenopus* tadpole retinas to $1\times10^{-5}$ M α-AAA produces selective alterations in Müller cell morphology and protein expression patterns. Although this concentration of α-AAA has no affect on the ability of photoreceptors to synthesize opsin, it does interfere with the ability of these cells to properly assembly nascent OS membranes. Following the model of OS morphogenesis proposed by Steinberg et al. (74), but without intending to be bound by theory, our results using α-AAA suggest that in the presence of a selective Müller cell inhibitor, photoreceptors are receiving improper signals for formation of the rims of individual outer segment discs.

To further investigate which retinal cell type is responsive to the stimulation of permissive glycans and its inhibition, we cultured RPE-deprived retinas with both $5\times10^{-5}$ M IPTG (the concentration that most effectively supports OS assembly), and $1\times10^{-5}$ M α-AAA (the concentration determined to have a specific inhibitory effect on Müller cells while not inhibiting photoreceptor synthesis of opsin). The results of this study demonstrated that the ability of the permissive glycan to promote OS assembly is severely diminished in the presence of the Müller cell inhibitor, thus strongly suggesting that Müller cells are key mediators of the observed organizational ability of permissive glycans (23). In the same study, we demonstrated that pigment epithelium derived factor (PEDF) is able to support proper membrane folding after inhibition of Müller cell metabolism by α-AAA, while IPTG requires intact Müller cell function. Thus, it appears that redundant mechanisms (both intrinsic and extrinsic) exist to support the ability of photoreceptors to properly assemble their OS. It is likely that the receptor for PEDF resides in the photoreceptors themselves, whereas that for permissive glycans is localized to Müller cells, which in turn communicate with photoreceptors to promote proper membrane assembly.

As discussed above, photoreceptor health is tightly linked to integrity to neighboring RPE and Müller cells (4, 10-12, 22, 76, 77). For example, the targeted disruption of Müller cell metabolism with α-AAA results in disorganization of photoreceptor OS, despite normal levels of opsin expression (22). It is believed that the glycan receptor that mediates these effects is localized to Muller cells.

The procedures outlined below provide further description of materials and methods useful in localizing the retinal glycan receptor.

1. Immunohistochemical localization of the glycan receptor. If by sequence identification of a particular glycan receptor it is determined that the receptor is a known protein for which an antibody is available through a commercial distributor, the antibody can be used to perform the studies outlined in this section. If, however, an antibody is not readily available, one (or more) antibodies can be generated using methods well known to those of skill in the art in a suitable animal such as a rabbit, goat, mouse, etc., e.g. using peptide sequences determined via MS/MS. A commercial polyclonal antisera production package from Sigma-Genosys, e.g., includes the following services: synthesis of the peptide (Ig purity, 10 mg, up to 15 amino acids); conjugation of the peptide to keyhole-limpet hemocyanin; immunization of two rabbits, six immunizations per rabbit; with four bleeds per rabbit. Typically, approximately 100-150 ml of serum is available for each antibody generated.

The specificity of the antibody is confirmed by Western blotting. Briefly, retinal extracts of equal total protein concentration are separated on 1-D SDS PAGE gels using standard protocols. The proteins are electroblotted to HyBondP membranes. Visualization of proteins is performed using. e.g., the ECF Western blotting kit (Amersham Biosciences), according to the manufacturer's specifications. The membrane is dried and scanned on a Typhoon 9400 Imaging Device at 560 nm.

The antibody should recognize a single molecular weight species at the identical relative molecular weight to that shown in Example 5 above (i.e., ~63 kD). To further confirm the specificity of an antibody directed against the glycan receptor, the antibody can be used to immunoprecipitate the receptor and determine its identity using LC/MS/MS.

To localize a retinal glycan receptor using an anti-glycan receptor antibody, retinas, e.g. from stage 33/34 *Xenopus laevis* tadpoles or from other suitable species, are fixed for two hours in 4% paraformaldehyde. Retinas are bisected or embedded in low melting point agarose followed by vibratome sectioning. Non-specific binding sites are blocked using 5% serum in PBS. Retinas are exposed to anti-glycan receptor primary antibody overnight. A suitable secondary antibody is an anti-rabbit antibody coupled to Alexa fluor 488 (Molecular Probes). Sections are mounted on glass slides with VectaShield Mounting Medium containing propidium iodide (Vector Laboratories), thus allowing for nuclei to be visualized in addition to the specific labeling of the primary antibody. Suitable controls include substitution of non-immune rabbit serum for primary antibody. Retinal sections are examined and microscopic images are acquired, e.g., using a Krypton-argon laser scanning confocal microscope (Bio-Rad MRC 1024).

2. Localization of the glycan receptor using biotinylated-NA3 probe. RPE-deprived retinas from stage 33/34 *Xenopus laevis* tadpoles are exposed to Niu-Twitty medium containing $10^{-7}$ M biotinylated-NA3 for 3 hours, followed by fixation in 4% paraformaldehyde. Control retinas are incubated in NA3+ $10^{-5}$ M IPTG to reveal non-specific binding of the NA3 ligand. Subsequent procedures are identical to those described above for immunohistochemical localization. In this instance, however, the following primary and secondary antibodies are utilized: anti-biotin, mouse IgG (Molecular Probes) as primary antibody; and anti-mouse chicken IgG labeled with Alexa Fluor 488 (Molecular Probes). To confirm the localization to a particular retinal cell type, sections are co-stained with antisera that are cell type-specific (e.g., directed against Müller cell- or photoreceptor-specific gene products).

Example 8

Knockdown of Retinal Glycan Receptor mRNA Using Antisense Oligonucleotides and Morpholinos This Example describes several approaches based on knockdown of the mRNA encoding a retinal glycan receptor protein. These strategies are useful, inter alia, to provide insights into the role of glycan receptors in photoreceptor OS assembly, e.g., to determine whether a particular retinal glycan receptor, isolated by the methods described herein, is sufficient to support photoreceptor OS assembly.

1. Antisense Oligonucleotides.

Antisense oligonucleotides are powerful tools to allow one to examine the function of a gene product by targeting the corresponding mRNA, thus generating a loss-of-function model in which to study the physiological role of the gene-of-interest (75). An antisense approach can be used to knock down a retinal glycan receptor of known sequence and to determine the effect of knocking down the receptor.

We have developed an assay system using intact isolated *Xenopus laevis* eye rudiments coupled with antisense oligonucleotides that is well suited to evaluating the functional role of specific gene products, e.g., in OS membrane assembly. As an example of the capability of this assay system, we generated a loss-of-function model for peripherin2, a genetically and phenotypically well-characterized gene (76-82). Photoreceptors of *Xenopus laevis* express three distinct isoforms of the peripherin2 gene; cones express xrds38 exclusively, whereas rods express xrds35, xrds36 and xrds38 (83). For purposes of validation of the antisense assay system, our evaluation was directed to xrds38.

Phosphorothioated oligonucleotides (two 20-base antisense oligonucleotides and one 20-base sense oligonucleotide) derived from the 5' end of the coding sequences of the xrds38 isoform of *Xenopus* peripherin2 were utilized. Additional controls included: retinas with an intact RPE, and retinas devoid of RPE with 5 mM exogenous lactose added to the medium. Neither of the control conditions included exposure to oligonucleotides. Eyes from stage 35/36 tadpoles were isolated and cultured in the presence of 1.5 µM oligonucleotide and 12 µg/ml Lipofectin for a pulse of four hours, followed by a 20 hour resting period, for a total duration of three and one-half days.

Examination of retinal morphology at the light microscopic level, concurrent with cellular uptake evaluation via confocal microscopic analysis, was used to monitor possible toxicity of an FITC-conjugated sense oligonucleotide. The percentage of retinal cells that had positive uptake of the FITC-conjugated oligonucleotide was determined by comparing the volume of bright to dark areas in optical sections obtained with the confocal microscope. Approximately 50% of the cells contained FITC-labeled oligonucleotide.

Referring to FIG. 10A, application of a sense oligonucleotide using this exposure paradigm resulted in no ultrastructural alterations of the photoreceptor cells. More specifically, outer segments were organized with the expected architecture of stacked flattened membranous saccules (compare FIG. 10A with FIGS. 1A and 1D). By contrast, antisense oligonucleotides complementary to peripherin2 negatively affected photoreceptor structure exclusively. Both antisense oligonucleotides complementary to peripherin2 produced dramatic alterations in photoreceptor structure. Under both conditions, the majority of photoreceptors were lacking both inner and outer segments. In some cells, photoreceptor OS were highly disorganized (FIGS. 10B, C). Both rod and cone photoreceptors were affected by the xrds38 antisense oligonucleotides, as expected for an isoform expressed by both photoreceptor types (83)

The steady-state levels of each protein were compared to the levels detected in control retinas maintained with an intact RPE cell layer. In retinas supported by lactose, the level of peripherin2 protein was slightly elevated above control (FIG. 10D), as previously described (62). In these same eyes, the amount of opsin was not significantly different from controls with an intact retina-RPE complex. Retinas exposed to the sense oligonucleotide expressed levels of peripherin2 and opsin proteins that were unchanged from control levels. On the contrary, retinas exposed to both forms of antisense oligonucleotide expressed drastically reduced levels of both peripherin2 and opsin. The peripherin2 protein was barely detectable and opsin was reduced to ~5% of control levels using our assay system (FIG. 10D).

These results demonstrate that application of antisense oligonucleotide technology can prevent normal photoreceptor OS membrane formation and promote the loss of inner segments in the majority of photoreceptors. A minority of photoreceptors had improperly folded OS with a disorganized structure, the morphology of which reflects that described in donor retinas affected with autosomal dominant retinitis pigmentosa due to mutations in the peripherin/RDS gene (82). The variability in photoreceptor OS structure may be due to the relative uptake of antisense oligonucleotide into the individual photoreceptors. Analysis of the protein levels indicates that the overall levels of both peripherin2 and opsin are drastically reduced compared to control retinas. The results in the *Xenopus* system are comparable to the protein levels reported in the rds mouse, in which a mutated truncated peripherin2 protein leads to instability in the OS structure. In the rds model, the opsin mRNA levels and synthesis rates are relatively high, i.e., 70% and 92% of normal, respectively. However, the steady-state level of the opsin protein levels are very low (~3% of normal), due to a high turnover rate (85).

2. Morpholinos. As an alternative to antisense oligonucleotides, morpholinos directed against the glycan receptor can be used to knock down the glycan receptor and study the effects thereof. Morpholinos have been used with success in Zebrafish and *Xenopus* to knock down gene function in a very specific manner (86-88). Morpholinos are short chains comprising a nucleic acid base, a morpholine ring and a non-ionic phosphorodiamidate intersubunit linkage. These molecules act via an RNAse H-independent steric block mechanism and can either block the translation initiation complex (by targeting the 5' UTR through the first 25 bases of coding sequence), or block the nuclear splicing machinery (by targeting splice junctions in pre-mRNA).

Morpholinos have high binding affinity for mRNA and exquisite specificity, which combine to yield reliable and predictable results. Because morpholinos lack a negatively charged backbone, they are less likely to interact nonspecifically with cellular proteins, which is a recognized phenomenon that can confound interpretation of results when using antisense oligonucleotides. Suitable controls for use with morpholinos include at least one mismatch and one scrambled control oligomer, as well as a dose-response study to differentiate toxic effects from specificity of the phenotype. Preferably, the levels of the target protein and several other control proteins are measured. Controls preferably further include a confirmation of the specificity of the phenotype by mRNA rescue (86).

Example 9

Isolation of Retinal Glycan Receptor Using Anti-Acridine Antibody

This Example describes a second procedure for isolating a glycan receptor, in this case based on affinity chromatography using an anti-acridine antibody to bind to an NA3 ligand tagged with aminoacridine.

1. Acquisition of *Xenopus laevis* retinal tissue. *Xenopus laevis* embryos are obtained essentially as described above. Briefly, embryos are obtained through induced breeding of adult frogs by injection of human chorionic gonadotropin. Embryos are staged by external morphologic criteria as described by Nieuwkoop and Faber (89). Eye rudiments are removed from stage 33/34 tadpoles. At this stage, the sclera-choroid layers have not yet enveloped the eye rudiments; therefore, the RPE is the outermost cell layer. Eyes removed from tadpoles at this stage are very responsive to permissive glycans (19, 23, 60, 62-64), confirming that the receptor is expressed and active in these animals. Lighting conditions are cyclic (12 hr light: 12 hr dark), provided by incandescent illumination equivalent to approximately 200-250 lux/m$^2$ at the level of the cultures (65).

2. Generation of AA-Ac-labeled NA3 ligand. Asialo, galactosylated, triantennary NA3 (V-Labs; >95% pure as demonstrated by MS and HPLC spectra) are tagged with AA-Ac ((3-(acetylamino)-6-aminoacridine), e.g., using the LudgerTag 2-AA-Ac Glycan Labeling Kit (Ludger) following the manufacturer's protocol. This kit contains reagents for the conjugation of AA-Ac dye to the free reducing end of glycans by a reductive animation reaction. Following labeling, the mixture is passed through a LudgerClean S Glycan Cleanup Cartridge (Ludger) following manufacturer's protocol, to remove any non-labeled glycan along with any unconjugated AA-Ac.

3. Isolation of the glycan receptor using immunoprecipitation and Blue Native gel electrophoresis. Three sets of RPE-deprived *Xenopus laevis* tadpole retinas are cultured, under one experimental condition, i.e., 10$^{-7}$ M AA-Ac-tagged NA3; and two control conditions, i.e. 10$^{-7}$ M AA-Ac-tagged NA3+ 10$^{-5}$ M IPTG as a competitive glycan; and Niu-Twitty medium alone. Each set of retinas includes four pools of about 1000 retinas, each from stage 33/34 *Xenopus* tadpoles. We have determined that each tadpole eye contains approximately 1 mg of total protein. Accordingly, this procedure provides ~4 mg total protein for each experimental condition.

Retinas are harvested after three hours of culture in AA-Ac-tagged NA3 and proteins are extracted using a NativePAGE Sample Prep Kit (Invitrogen) according to manufacturer's instructions. This kit contains two detergents (10% n-dodecyl-β-D-maltoside) that improve the solubility of hydrophobic and membrane proteins during sample preparation.

Extracted proteins are applied to a Protein G slurry to which anti-acridine antibodies (Cerus Corporation) have been coupled. After four hours of rocking at 4° C., the uncoupled proteins are removed by centrifugation. Proteins coupled to the anti-acridine antibodies are extracted using NativePAGE 4× Sample Buffer. Immediately prior to loading samples on NativePAGE™ Novex® 3-12% Bis-Tris Gels, G-250 Sample Additive is added according to manufacturer's specifications (Invitrogen). Gels are stained with Sypro ruby to visualize protein bands.

In-gel digestion of proteins and LC/MS/MS. The band(s) identified as the permissive glycan receptor are excised and subjected to tryptic digestion followed by liquid chromatography/mass spectrometric (i.e., LC/MS/MS) analysis of the tryptic peptides using the previously published protocols of Giorgianni et al. (93). Briefly, the purified glycan receptor is mixed with sequencing grade trypsin (Promega). Digestion is carried out overnight (37° C.), and stopped by the addition of acetic acid (final pH 3.0). The tryptic peptides are manually loaded onto a capillary C18 PicoFrit column (New Objective), packed with 9-10 cm of C18 silica-based reversed-phase packing material (200A MAGIC C18) from Michrom Bioresources. Column packing is carried out under nitrogen gas pressure (400-500 psi) with a homemade pressure-vessel. Samples are analyzed with a gradient-elution program that consists of a 5-min initial isocratic elution with 0% B; a linear gradient 0-70% B in 60 min (1.05% acetonitrile min-1); 5-min isocratic elution with 70% B; and a linear gradient 70-0% B in 10 min (A=water-0.1% formic acid. B=90% acetonitrile-10% water-0.1% formic acid).

Peptides are eluted at a 100 nL/min flow rate, and introduced online into a nanoESI-quadrupole ion-trap MS ($LCQ^{Deca}$, ThermoFinnigan). The instrument is set to execute one MS scan followed by a zoom scan of the most intense peptide signal, and by an MS/MS scan of each one of the four most intense peaks from the MS scan. The MS/MS data (.dta files) are searched against the vertebrate protein subset obtained from the SwissPROT protein sequence database, with the search engine SEQUEST (94) that is part of the $LCQ^{Deca}$ software package.

Example 10

Mouse Models for Testing Permissive Glycans as Therapeutic Agents for Inherited Retinal Degenerations and Age-Related Macular Degeneration $Crb1^{rd8}/Crb1^{rd8}$ mouse model of RP and Leber's disease. The Crumbs protein in *Drosophila* has shed light on the role of adherens junctions in cell and tissue organization. In highly polarized photoreceptors, the Crumbs complex is localized to the subapical region, which is adjacent to the adherens junctions. In *Drosophila*, Crumbs plays a role in both supporting the formation of the adherens junctions and promoting elongation of the rhabdomere (the fly equivalent of the mammalian outer segment). In humans, the orthologous gene has been isolated and named CRBI. Mutations in CRBI have been shown to cause Leber congenital amaurosis (103) and retinitis pigmentosa (104).

The mutant $Crb1^{rd8}/Crb1^{rd8}$ mouse is a spontaneous mutant in which a deletion of a single base pair results in a frame shift, leading to truncation of the protein and loss of function (105). Histologically, the retina of the $Crb1^{rd8}/Crb1^{rd8}$ mouse features intermittent, but not total, loss of adherens junctions at the outer limiting membrane. The loss of adherens junctions is coexistent with shortened inner and outer segments and focal degenerative loss of photoreceptors (105). As such, $Crb1^{rd8}/Crb1^{rd8}$ mice provide an excellent model for testing the ability of permissive glycans to promote the formation of adherens junctions in the retina and thus promote normal cellular cytoarchitecture which is likely to be required for normal outer segment membrane assembly and stability in the photoreceptors. $Crb1^{rd8}/Crb1^{rd8}$ mice (Stock Number 003392) and C57BL/6J control mice (Stock Number 000664) are commercially available from The Jackson Laboratory.

$Ccl2^{-/-}/Cx3cr1^{-/-}$ knockout mouse model of AMD. As discussed, a mouse model of AMD has been recently developed which is a double knockout of CCL2 (Chemokine (C—C motif) ligand 2 and CX3CR1, a chemokine receptor (102). CCL2 is known to play an immunoregulatory role in the pathology of AMD. Single nucleotide polymorphisms of CX3CR1 are associated with AMD. Conveniently, the combination of knocking out both of these genes results in a phenotype in which features of AMD rapidly appear. By 1.5 months, 100% of $Ccl2^{-/-}/Cx3cr1^{-/-}$ mice develop many of the cardinal pathologies associated with AMD, including drusen formation, RPE pathology and photoreceptor demise (102). The pathology in the photoreceptors includes improperly folded outer segment membranes. Theses features of the $Ccl2^{-/-}/Cx3cr1^{-/-}$ mouse thus make it an excellent model for testing various therapeutic options for the treatment of AMD.

Testing of candidate permissive glycans as therapeutics for retinal diseases. In vitro toxicity studies of a candidate glycan compound can be carried out using intact eyes from *Xenopus laevis*. In vivo safety and efficacy can be assessed, e.g., using a mouse model of retinal degeneration or AMD such as the above-described $Crb1^{rd8}/Crb1^{rd8}$ or $Ccl2^{-/-}/Cx3cr1^{-/-}$ mouse models, or other naturally occurring or mechanically induced models of AMD that are known in the art, such as a laser-induced model of neovascularization.

For example, a test compound (e.g., 2 µl of NA3 solubilized in PBS) is injected into the superior temporal quadrant of the left eye of $Crb1^{rd8}/Crb1^{rd8}$ mice and the uninjected right eyes serve as controls. Other controls can include injection of PBS alone or other compositions as appropriate. Clinical examinations are subsequently performed at various intervals after injection. Examinations carried out in the living animals can include one or more of the following: slit lamp examination, indirect opthalmoscopic examination, fundus photography, and electroretinography (ERG). After sacrifice of the mice, one or more of the following laboratory studies are performed: histological assessment; TUNEL staining; immunohistochemistry and optionally, electron microscopy.

For toxicity studies, clinical testing as described is commenced e.g. at day 1 after injection and is continued. e.g., daily for 3-5 days and then twice per week for up to two months. If signs of toxicity appear, the dose of the administered compound is decreased and the protocol is repeated. If no signs of toxicity are observed by clinical examination, laboratory studies are performed in groups of mice, e.g., at 3 weeks and 6 weeks post-injection.

By fundus examination, the retina of the $Crb1^{rd8}/Crb1^{rd8}$ mouse is known to exhibit multiple white spots which correspond at the microscopic level with the formation of rosettes. By histology, the retina of the $Crb1^{rd8}/Crb1^{rd8}$ mouse presents with intermittent, but not total loss of adherens junctions, which is localized to areas of the retina having shortened inner and outer segments and focal degenerative loss of the photoreceptors. Accordingly, the efficacy of a candidate permissive glycan administered to the retina of a $Crb1^{rd8}/Crb1^{rd8}$ mouse can be assessed by various means generally known in the art and as described more particularly below, to determine if the test compound can promote adherens junctions formation, prevent the loss of photoreceptors and otherwise support overall retinal structure.

Detailed procedures for laboratory exams. For structural analysis, eyes from the mouse models are enucleated after marking the superior border of the eye and immersion fixed for 24 hours in a mixed aldehyde fixative (e.g., 2% paraformaldehyde, 2% glutaraldehyde in 0.1M phosphate buffer). Eyes are processed using standard techniques and embedded in Epon Araldite, as we have described previously (106). Eyes are oriented such that when cut, sections will contain the superior and inferior quadrants and will include the optic nerve. Sections are viewed on a Nikon Eclipse E800 photomicroscope with a Sensys camera.

To evaluate the extent of retinal disease or rescue, a protocol such as that of Paskowitz et al. (107) is used to analyze photoreceptors as the number of cells per area of outer nuclear layer. This method is preferred because of the discontinuous area of photoreceptor loss in the Crb1$^{rd8}$/Crb1$^{rd8}$ mouse. Photoreceptor survival and inner/outer segment length are evaluated in six points in each eye, three in the superior and three in the inferior quadrants.

For ultrastructural analysis, areas of interest selected from plastic-embedded thick sections are thin sectioned and placed on 200 mesh copper grids. Sections are viewed on a JEOL JEM1200EX II electron microscope, as we have described (106).

For immunohistochemical localization of antigens of interest, eyes are enucleated at specified times and immersion fixed for 24 hours in 2% paraformaldehyde in 0.1M phosphate buffer. The anterior segment and lens are removed and the remaining eyecup is embedded in OCT embedding compound. Frozen sections of 12 µm thickness are prepared.

TUNEL staining is performed using DeadEnd Fluorometric TUNEL System following the manufacturer's recommendations.

Immunohistochemistry is performed using standard techniques. The appropriate fluorescently tagged secondary antibody is utilized in conjunction with each primary antibody. Nuclear layers are labeled with ToPro III idodide. Sections are viewed on a C1plus Modular Confocal Microscope (Nikon). Table 2 below provides a listing of suitable primary antibodies for use in the immunohistochemical studies.

Detailed procedures for clinical exams. To perform clinical exams, mice are lightly anesthetized with an intraperitoneal injection of Avertin. The anterior segment of the eye is examined using a Zeiss slit-lamp biomicroscope. Images of these structures are recorded with a Canon GL1 digital video camera via a video adapter. The cornea is examined for clarity and possible neovascularization. The lens is examined for clarity, and the iris is evaluated for depigmentation or inflammation.

TABLE 2

Antibodies for Assessing Efficacy of Compounds to Promote Retinal Integrity

| Antibody | Source | Purpose |
| --- | --- | --- |
| Anti-GFAP | Abcam ab38558 Polyclonal Antibody, Unconjugated | General retinal stress via GFAP upregulation of Müller cells |
| Anti-Crb1 | Santa Cruz sc-22737 Polyclonal Antibody, Unconjugated | Localization of crb1 |
| Anti-β catenin | Abcam ab23512 Polyclonal antibody, unconjugated | Localization of adherens junction |
| Anti-pan cadherin | Invitrogen 71-7100 Polyclonal Antibody, unconjugated, | Localization of adherens junction |

Example 11

Screening for Modulators of Retinal Glycan Receptors

In addition to the disclosed multivalent N-linked glycans, other compounds that bind the retinal glycan receptor identified herein (i.e, "modulators of the glycan receptor") can be identified by the methods set forth herein, and such modulators are potentially useful for the treatment and prevention of diseases and disorders of the eye and particularly the retina.

Screening assays as described above can be used to identify modulators of the glycan receptors. One such screening assay is the *Xenopus laevis* system that allows for convenient in vito analysis of OS membrane formation and thus is useful for large-scaled testing of the efficacy of various compounds on OS membrane formation (see, e.g., Example 1).

To test a candidate agent, intact retinas are removed from stage 33/34 *Xenopus laevis* tadpoles and placed into culture in Niu-Twitty medium for three days. These retinas are contacted by a test agent and the ability to induce proper formation of the OS membrane is evaluated as described above. As a positive control, $5 \times 10^{-3}$ M lactose is used. Promising compounds showing evidence of efficacy in the *Xenopus* system are subjected to further in vivo testing in mouse models of retinal diseases, as described above, e.g., in Example 10.

Once a candidate glycan receptor modulator is identified by the methods set forth above, these modulators can be further optimized using, e.g., rational drug design.

REFERENCES

It is believed that a review of the references will increase appreciation of the present invention. The following documents are referred to throughout the present disclosure by a number, as indicated below.

1. Young R W. The renewal of photoreceptor cell outer segments. J. Cell Biol. 1967; 33:61-72.
2. De Robertis E. Some observations on the ultrastructure and morphogenesis of photoreceptors. J. Gen. Physiol. 1956; 43:1-13.
3. Cohen A I. New evidence supporting the linkage to extracellular space of outer segment saccules of frog cones but not rods. J. Cell Biol. 1968; 37:424-444.
4. Hollyfield J G, Witkovsky P. Pigmented retinal epithelium involvement in photoreceptor development and function. J. Exp. Zool. 1974; 189:357-378.
5. Sheedlo H J, Linxi L. Turner J E. Effects of RPE-cell factors secreted from permselective fibers on retinal cells in vitro. Brain Res. 1992; 587:327-337.
6. Gaur V P. Liu Y. Turner J E. RPE conditioned medium stimulates photoreceptor cell survival, neurite outgrowth and differentiation in vitro. Exp. Eye Res. 1992; 54:645-659.
7. Sheedlo H J, Nelson T H, Lin N, Rogers T A, Roque R S, Turner J E. RPE secreted proteins and antibody influence photoreceptor cell survival and maturation. Brain Res. Dev. Brain Res. 1998:107:57-69.
8. Jablonski M M, Tombran-Tink J, Mrazek D A, Iannaccone A. Pigment epithelium-derived factor supports normal development of photoreceptor neurons and opsin expression after retinal pigment epithelium removal. J. Neurosci. 2000; 20:7149-7157.
9. Jablonski M M, Tombran-Tink J, Mrazek D A, Iannaccone A. Pigment epithelium-derived factor supports normal Müller cell development and glutamine synthetase expression after removal of the RPE. Glia 2001; 35:14-25.
10. Reichenbach A, Stolzenburg J-U, Eberhardt W, Chao T I, Dettmer D, Hertz L. What do retinal Müller (glial) cells do for their neuronal 'small siblings'? J. Chem. Neuroanat. 1993; 6:201-213.
11. Cao W, Wen R. Li F. Cheng T, Steinberg R H. Induction of basic fibroblast growth factor mRNA by basic fibroblast growth factor in Muller cells. Invest Opthalmol V is Sci 1997; 38(7): 1358-66.
12. Newman E, Reichenbach A. The Müller cell: A functional element of the retina. Trends Neurosci 1996; 19:307-312.

13. Ullian E M, Sapperstein S K, Christopherson K S, Barres B A. Control of synapse number by glia. Science 2001; 291:657-661.
14. Ullian E M, Christopherson K S, Barres B A. Role for Glia in Synaptogenesis. Glia 2004; 47:209-216.
15. Newman E. Glial Modulation of Synaptic Transmission in the Retina. Glia 2004; 47:268-274.
16. Araque A, Perea G. Glial Modulation of Synaptic Transmission in Culture. Glia 2004; 47:241-248.
17. Turner D L. Cepko C L. A common progenitor for neurons and glia persists in rat retina late in development. Nature 1987; 328:131-136.
18. Robinson S R, Dreher Z. Müller cells in adult rabbit retinae: Morphology, distribution and implications for function and development. J. Comp. Neurol. 1990; 292: 178-192.
19. Jablonski M M, Ervin C S. A closer look at lactose-mediated support of retinal morphogenesis. Anat. Rec. 2000; 259:205-214.
20. Tepass U. Adherens junctions: new insight into assembly, modulation and function. Bioessays 2002; 24(8):690-5.
21. Reichenbach A, Faude F, Enzmann V, Bringmann A, Pannicke T, Francke M, et al. The Müller (glial) cell in normal and diseased retina: a case for single-cell electrophysiology. Ophthalmic Res 1997; 29:326-340.
22. Jablonski M M, Iannaccone A. Targeted disruption of Müller cell metabolism induces photoreceptor dysmorphogenesis. Glia 2000; 32: 192-204.
23. Wang X F, Iannaccone A, Jablonski M M. Contribution of Muller cells toward the regulation of photoreceptor outer segment assembly. Neuron Glia Biol. 2005; 1(1-6).
24. Ozaki K, Lee R T, Lee Y C, Kawasaki T. The differences in structural specificity for recognition and binding between asialoglycoprotein receptors of liver and macrophages. Glycoconj J 1995; 12(3):268-74.
25. Sato M, Nishi N, Shoji H, Seki M, Hashidate T, Hirabayashi J, et al. Functional analysis of the carbohydrate recognition domains and a linker peptide of galectin-9 as to eosinophil chemoattractant activity. Glycobiology 2002; 12(3):191-7.
26. Brown G D. Taylor P R, Reid D M, Willment J A, Williams D L, Martinez-Pomares L. et al. Dectin-1 is a major beta-glucan receptor on macrophages. J. Exp. Med. 2002; 196: 407-412.
27. Debenham S D, Snyder P W, Toone E J. Solid-phase synthesis for the identification of high-affinity bivalent lectin ligands. J Org Chem 2003; 68(15):5805-11.
28. Maier M A, Yannopoulos C G, Mohamed N, Roland A, Fritz H, Mohan V, et al. Synthesis of antisense oligonucleotides conjugated to a multivalent carbohydrate cluster for cellular targeting. Bioconjug Chem 2003; 14(1):18-29.
29. Brown G D, Herre J. Williams D L, Willment J A, Marshall A S, Gordon S. Dectin-1 mediates the biological effects of beta-glucans. J. Exp. Med. 2003; 197:1119-1124.
30. Herre J. Gordon S, Brown G D. Dectin-1 and its role in the recognition of beta-glucans by macrophages. Mol. Immunol. 2004; 40:869-876.
31. Lee Y C. Binding modes of mammalian hepatic Gal/GalNAc receptors. Ciba Found. Symp. 1989; 145:80-93.
32. Yamamoto K, Ishida C, Shinohara Y, Hasegawa Y, Konami Y, Osawa T, et al. Interaction of immobilized recombinant mouse C-type macrophage lectin with glycopeptides and oligosaccharides. Biochemistry 1994; 33:8159-8166.
33. Garate M. Cao Z. Bateman E, Panjwani N. Cloning and characterization of a novel mannose-binding protein of Acanthamoeba. J. Biol. Chem. 2004; 279:29849-29856.
34. Winkler B S. Arnold M J, Brassell M A, Sliter D R. Glucose dependence of glycolysis, hexose monophosphate shunt activity, energy status, and the polyol pathway in retinas isolated from normal (nondiabetic) rats. Invest Opthalmol V is Sci 1997; 38(1):62-71.
35. Fliesler S J, Richards M J, Miller C Y, McKay S, Winkler B S. In vitro metabolic competence of the frog retina: effects of glucose and oxygen deprivation. Exp Eye Res 1997; 64(5):683-92.
36. Fliesler S J, Rayborn M E, Hollyfield J G. Membrane morphogenesis in retinal rod outer segments: inhibition by tunicamycin. J. Cell Biol. 1985; 100:574-587.
37. Defoe D M, Besharse J C, Fliesler S J. Tunicamycin-induced dysgenesis of retinal rod outer segment membranes. I. Quantitative freeze-fracture analysis. Invest. Opthalmol. Vis. Sci. 1986; 27:1595-1601.
38. Ulshafer R J, Allen C B, Fliesler S J. Tunicamycin-induced dysgenesis of retinal rod outer segment membranes. II. A scanning electron microscopy study. Invest. Opthalmol. Vis. Sci. 1986; 27:1587-1594.
39. Fliesler S J, Rayborn M E, Hollyfield J G. Inhibition of oligosaccharide processing and membrane morphogenesis in retinal rod photoreceptor cells. Proc. Natl. Acad. Sci. 1986; 83:6435-6439.
40. Joubert R. Caron M, Bladier D. Investigation on the occurrence of soluble lectins in mammalian nervous tissue extracts. Comparative Biochemistry and Physiology. B: Comparative Biochemistry 1986; 85(4):859-63.
41. Kivela T. Characterization of galactose-containing glycoconjugates in the human retina: a lectin histochemical study. Current Eye Research 1990; 9(12): 1195-209.
42. Castagna L F, Landa C A. Distribution of an endogenous 16-kd S-lac lectin in the chicken retina. Investigative Ophthalmology and Visual Science 1994; 35(13):4310-6.
43. Castagna L F, Landa C A. Isolation and characterization of a soluble lactose-binding lectin from postnatal chicken retina. Journal of Neuroscience Research 1994; 37(6):750-8.
44. Bridges C D B, Fong S L. Different receptor for distribution of peanut and ricin agglutinin between inner and outer segments of rod cells. Nature 1979; 282:513-515.
45. Varner H H, Rayborn M E, Osterfeld A M, Hollyfield J G. Localization of proteoglycan within the matrix sheath of cone photoreceptors. Exp. Eye Res. 1987; 44:633-642.
46. Tawara A. Varner H H, Hollyfield J G. Proteoglycans in the mouse interphotoreceptor matrix. II. Origin and development of proteoglycans. Exp. Eye Res. 1989; 48:815-839.
47. Lahiri D, Hollyfield J G. Development of WGA-binding domains in the IPM of *Xenopus laevis* embryos. Invest. Opthalmol. Vis. Sci. (Suppl.) 1992; 33(4):815.
48. Maldonado C A, Castagna L F, Rabinovich G A, Landa C A. Immunocytochemical study of the distribution of a 16-kDa galectin in the chicken retina. Invest Opthalmol V is Sci 1999;40(12):2971-7.
49. Uehara F, Ohba N, Ozawa M. Isolation and Characterization of Galectins in the Mammalian Retina. Invest. Opthalmol. Vis. Sci. 2001; 42:2164-2172.
50. Sato Y. Liu C, Wojczyk B S, Kobata A, Spitalnik S L, Endo T. Study of the sugar chains of recombinant human amyloid precursor protein produced by Chinese hamster ovary cells. Biochem Biophys Acta 1999; 1472:344-358.
51. Bezouska K, Krajhanzl A, Pospisil M, Kubrycht J, Stajner K, Felsberg J, et al. Characterization of the high-affinity oligosaccharide-binding site of the 205-kDa porcine large 51. granular lymphocyte lectin, a member of the leukocyte common antigen family. Er. J. Biochem. 1993; 213:1303-1313.
52. Gupta D. Sourolia A. Synthesis of neoglycopeptides and analyses of their biodistribution in vivo to identify tissue specific uptake and novel putative membrane lectins. Glycoconj J 1994; 11:558-571.
53. Chiu M H. Thomas V H, Stubbs H J, Rice K G. Tissue targeting of multivalent Le(x)-terminated N-linked oligosaccharides in mice. J. Biol. Chem. 1995; 270:24024-24031.
54. Hayase T, Rice K G, Dziegielewska K M, Kuhlenschmidt M, Reilly T, Lee Y C. Comparison of N-glycosides of fetuins from different species and human alpha 2-HS-glycoprotein. Biochemistry 1992; 9:897-906.
55. Townsend R R, Hardy M R, Cumming D A, Carver J P, Bendiak B. Separation of branched sialyated oligosaccharides using high-pH anion-exchange chromatography with pulsed amperometric detection. Anal Biochem 1989; 182: 1-8.
56. Kitchener P D, Dziegielewska K M, Hutton E J, Hinrichsen C F, Saunders N R. Fetuin in neurons of the retina and cerebellum during fetal and postnatal development of the rat. Int. J. Dev. Neurosci. 1999; 17:21-30.
57. Sheedlo H J, Krishnamoorthy R S, Nelson T S, Agarwal N S, Liu J S, Roque R S, et al. Retina-derived fetuin (RDF): analysis by immunocytochemistry, reverse transcriptase-polymerase chain reaction and Southern blot. Curr. Eye Res. 1999; 19(465-471).
58. Wadhwa M S. Knoell D L, Young A P, Rice K G. Targeted gene delivery with a low molecular weight glycopeptide carrier. Bioconjug. Chem. 1995; 6:283-291.
59. Jablonski M M. The intact *Xenopus laevis* eye rudiment: A quasi-in vivo system for the study of retinal development and degenerations. Adv. Exp. Med. Biol. 2003; 533:189-196.
60. Stiemke M M, Hollyfield J G. Outer segment disc membrane assembly in the absence of the pigment epithelium: The effect of exogenous sugars. Dev. Brain Res. 1994; 80:285-289.
61. Stiemke M M, Hollyfield J G. Effect of sugars on photoreceptor outer segment assembly. In: Anderson R E, Hollyfield J G, LaVail M M, editors. Degenerative Diseases of the Retina. New York: Plenum Publishing Corp.; 1995. p. 129-137.
62. Jablonski M M, Wohabrebbi A, Ervin C S. Lactose promotes organized photoreceptor outer segment assembly and preserves expression of photoreceptor proteins in retinal degeneration. Mol. Vis. 1999; 5:16.
63. Jablonski M M, Iannaccone A. Lactose supports Müller cell protein expression patterns in the absence of the retinal pigment epithelium. Mol. Vis. 2001; 7:27-35.
64. Wang X F, Iannaccone A, Jablonski M M. Permissive glycan support of photoreceptor outer segment assembly occurs via a non-metabolic mechanism. Mol. Vis. 2003; 9:701-709.
65. Stiemke M M, Landers R A, Al-Ubaidi M R, Hollyfield J G. Photoreceptor outer segment development in *Xenopus laevis*: Influence of the pigment epithelium. Dev. Biol. 1994; 162:169-180.
66. Jablonski M M, Iannaccone A, Wang X F. Lactose support of photoreceptor outer segment assembly demonstrates characteristics of a receptor-mediated phenomenon. Association for Research in Vision and Opthalmology 2002; Annual Meeting Abstract and Program Planner [on CD-ROM]: Abstract 3737.
67. Jablonski M M, Graney M J, Kritchevsky S B, Iannaccone A. Reliability assessment of a rod photoreceptor outer segment grading system. Exp. Eye Res. 2001; 72:573-579.
68. Cho S. Scharpf S, Franko M, Verneulen C W. Effect of iso-propyl-thio-beta-D-galactoside concentration on the level of lac-operon induction in steady state *Escherichia coli*. Biochem Biophys Res Commun 1985; 128:1268-1273.
69. Lund Karlsen R, Pedersen O O, Schousboe A, Langeland A. Toxic effects of DL-a-aminoadipic acid on Müller cells from rats in vivo and cultured cerebral astrocytes. Exp. Eye Res. 1982; 35:305-311.
70. Olney N W, Ho O L, Rhee V. Cytotoxic effects of acidic and sulphur containing amino acids on the infant mouse central nervous system. Exp. Brain Res. 1971; 14:61-76.
71. Rich K A, Figueroa S L, Zhan Y, Blanks J C. Effects of Muller cell disruption on mouse photoreceptor cell development. Exp Eye Res 1995; 61(2):235-48.
72. Garthwaite J, Regan C M. Toxic effects of alpha-aminoadipate and cultured cerebellar cells. Brain Res. 1980; 194: 603-607.
73. Huck S, Grass F, Hortnagl H. The glutamate analogue alpha-aminoadipic acid is taken up by astrocytes before exerting its gliotoxic effect in vitro. J. Neurosci. 1984; 4:2650-2657.
74. Steinberg R H, Fisher S K, Anderson D H. Disc morphogenesis in vertebrate photoreceptors. J. Comp. Neurol. 1980; 190:501-518.
75. Brysch W. Schlingensiepen K H. Design and application of antisense oligonucleotides in cell culture, in vivo and as therapeutic agents. Cell and Molec. Neurobiol. 1994; 14:557-568.
76. Travis G H, Sutcliffe J G, Bok D. The retinal degeneration slow (rds) gene product is a photoreceptor disc membrane-associated glycoprotein. Neuron 1991; 6:61-70.
77. Arikawa K, Molday L L, Molday R S, Williams D S. Localization of peripherin/rds in the disk membranes of cone and rod photoreceptors: Relationship to disk membrane morphogenesis and retinal degeneration. J. Cell Biol. 1992; 116:659-667.
78. Bhatia P K, Travis G H. Rds/peripherin and rom-1: A new class of adhesion molecules. Invest. Opthalmol. Vis. Sci. 1994; 35 (Suppl.):2675.
79. Sanyal S, Chader G. Aguirre G. Expression of retinal degeneration slow (rds) gene in the retina of the mouse. New York: Alan R. Liss Inc.; 1985.
80. Usukura J, Bok D. Changes in the localization and content of opsin during retinal development in the rds mutant mouse: Immunocytochemistry and immunoassay. Exp. Eye Res. 1987; 45:501-515.
81. Hawkins R K, Jansen H G, Sanyal S. Development and degeneration of retina in rds mutant mice: photoreceptor abnormalities in the heterozygotes. Exp. Eye Res. 1985; 41:701-720.
82. Flannery J G. Farber D B, Bird A C, Bok D. Degenerative changes in a retina affected with autosomal dominant retinitis pigmentosa. Invest. Opthalmol. Vis. Sci. 1989; 30:191-211.
83. Kedzierski W. Moghrabi W N, Allen A C, Jablonski-Stiemke M M, Azarian S, Bok D, et al. Three homologs of rds/peripherin in *Xenopus laevis* photoreceptors that exhibit covalent and non-covalent interactions. J. Cell Sci. 1996; 109:2551-2560.
84. Jablonski M M. Investigating the mechanisms of retinal degenerations with antisense oligonucleotides. Doc. Opthalmol. 2001; 102:179-196.

85. Agarwal N, Nir I, Papermaster D S. IRBP gene expression in the dystrophic retina of the mutant rds mouse. In: Anderson R E, Hollyfield J G, LaVail M M, editors. Retinal Degenerations. Boston: CRC Press, 1991.
86. Ekker S C. Morphants: a new systematic vertebrate functional genomics approach. Yeast 2000; 17:302-306.
87. Zhang C, Basta T, Klymkowsky M W. SOX7 and SOX18 are essential for cardiogenesis in *Xenopus*. Dev Dyn 2005; 234:878-891.
88. Martin B L, Harland R M. A novel role for lbx1 in *Xenopus* hypaxial myogenesis. Development 2006; 14(133): 195-208.
89. Nieuwkoop P D, Faber J. Normal Table of *Xenopus laevis* (Daudin). Amsterdam: North Holland Publishing Co.; 1956.
90. Saha S K, Brewer C F. Determination of the concentrations of oligosaccharides, complex type carbohydrates, and glycoproteins using the phenol-sulfuric acid method. Carbohydr Res 1994; 254: 157-67.
91. Wissing J, Helm S, GFlohe L, Billtewski U, Frank R. Enrichment of hydrophobic proteins via Triton X-114 phase partitioning and hydroxyapatite column chromatography for mass spectrometry. Electrophoresis 2000; 21:2589-2593.
92. Wohabrebbi A, Umstot E S, Iannaccone A, Desiderio D M, Jablonski M M. Downregulation of a novel photoreceptor protein correlates with improper outer segment assembly. J. Neurosci. Res. 2002; 67:298-308.
93. Giorgianni F, Beranova-Giorgianni S, Desiderio D M. Identification and characterization of phosphorylated proteins in the human pituitary. Rapid Commun. Mass Spectrom. 2003; in press.
94. Yates J R, 3rd, Eng J K, McCormack A L. Mining genomes: correlating tandem mass spectra of modified and unmodified peptides to sequences in nucleotide databases. Anal Chem 1995; 67(18):3202-10.
95. Guérin C J. Lewis G P, Fisher S K, Anderson D H. Recovery of photoreceptor outer segment length and analysis of membrane assembly rates in regenerating primate photoreceptor outer segments. Invest. Opthalmol. Vis. Sci. 1993; 34:175-183.
96. Faktorovich E G, Steinberg R H, Yasumura D, Matthes M T, LaVail M M. Photoreceptor degeneration in inherited retinal dystrophy delayed by basic fibroblast growth factor. Nature 1990; 347:83-86.
97. Kancherla V, Kedzierski W, Travis G H, Jablonski M M. Abnormal formation of outer segments in *Xenopus laevis* eye rudiments cultured with rds antisense oligonucleotides. In: Hollyfield J G, Anderson R E, LaVail M M, editors. Retinal Degenerative Disease and Experimental Therapy. New York: Plenum Publishing; 1999. p. 419-429.
98. Lewis M L. Clinical presentations of AMD. In: Hampton G R. Nelsen P T, editors. Age-Related Macular Degeneration: Principles and Practice. New York: Raven Press; 1992. p. 137-81.
99. Zarbin M, Szirth B. Current treatment of age-related macular degeneration. Optom V is Sci. 2007; 84:559-72.
100. Donoso L A, Kim D, Frost A, Callahan A, Hageman G. The role of inflammation in the pathogenesis of age-related macular degeneration. Surv Opthalmol. 2006 March-April; 51(2): 137-52.
101. Anderson D H, Mullins R F, Hageman G S, Johnson L V. A role for local inflammation in the formation of drusen in the aging eye. Am J. Opthalmol. 2002 September: 134(3): 411-31.
102. Tuo J. Bojanowski C M, Zhou M, Shen D, Ross R J, Rosenberg K I, et al. Murine ccl2/cx3cr1 deficiency results in retinal lesions mimicking human age-related macular degeneration. Invest Opthalmol V is Sci. 2007; 48:3827-36.
103. Lotery A J, Jacobson S G, Fishman G A, Weleber R G, Fulton A B, Namperumalsamy P, et al. Mutations in the CRB1 gene cause Leber congenital amaurosis. Arch Opthalmol. 2001 March; 119(3):415-20.
104. Lotery A J, Malik A, Shami S A, Sindhi M, Chohan B, Maqbool C, et al. CRB1 mutations may result in retinitis pigmentosa without para-arteriolar RPE preservation. Ophthalmic Genet. 2001 September; 22(3): 163-9.
105. Mehalow A K, Kameya S. Smith R S, Hawes N L, Denegre J M, Young J A, et al. CRB1 is essential for external limiting membrane integrity and photoreceptor morphogenesis in the mammalian retina. Hum Mol Genet. 2003 Sep. 1; 12(17):2179-89.
106. Jablonski M M, Dalke C, Wang X F, Lu L, Manly K F, Pretsch W, et al. An ENU-induced mutation in Rs1h causes disruption of retinal structure and function. Mol Vis. 2005; 11:569-81.
107. Paskowitz D M, Donohue-Rolfe K M, Yang H, Yasumura D, Matthes M T, Hosseini K, et al. Neurotrophic factors minimize the retinal toxicity of verteporfin photodynamic therapy. Invest Opthalmol V is Sci. 2007; 48:430-7.

INCORPORATION BY REFERENCE

Patents, patent applications, and non-patent documents or references that are cited in this text, either in a Reference List before the claims, or in the text itself, including any manufacturer's specifications, instructions, etc. ("herein-cited references") are hereby expressly incorporated herein by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method of treating age-related macular degeneration, comprising administering to a subject in need thereof a therapeutically effective amount of a pharmaceutical composition comprising a multivalent N-linked oligosaccharide having the formula $(Gal-GlcNAc)_n-Man_3-GlcNAc_2$, where n is 1-4.

2. The method of claim 1, wherein said administration of the multivalent N-linked oligosaccharide composition promotes formation of photoreceptor outer segment membranes.

3. The method of claim 1, wherein said administration of the multivalent N-linked oligosaccharide composition promotes integrity of adherens junctions in the retina.

4. The method of claim 1, wherein the oligosaccharide is a biantennary N-linked oligosaccharide.

5. The method of claim 4, wherein the oligosaccharide is selected from the group consisting of an asialo, galactosylated, biantennary (NA2) oligosaccharide, an asialo, galactosylated, fucosylated, biantennary (NA2F) oligosaccharide, and a disialo, galactosylated, biantennary (A2) oligosaccharide.

6. The method of claim 1, wherein the oligosaccharide is a triantennary N-linked oligosaccharide.

7. The method of claim 6, wherein the oligosaccharide is selected from the group consisting of an asialo, galactosylated, triantennary (NA3) oligosaccharide, and a trisialo, galactosylated, triantennary (A3) oligosaccharide.

8. The method of claim 1, wherein the oligosaccharide is a tetraantennary N-linked oligosaccharide.

9. The method of claim 8, wherein the oligosaccharide is an asialo, galactosylated tetraantennary (NA4) oligosaccharide.

10. The method of claim 1, wherein the form of age-related macular degeneration is the wet form.

11. The method of claim 1, wherein the form of age-related macular degeneration is the dry form.

12. The method of claim 1, wherein the composition is administered to the eye of the subject.

13. The method of claim 12, wherein the composition is administered by intraocular injection.

* * * * *